United States Patent [19]
Haff et al.

[11] Patent Number: 5,827,480
[45] Date of Patent: Oct. 27, 1998

[54] NUCLEIC ACID AMPLIFICATION REACTION APPARATUS

[75] Inventors: Lawrence A. Haff, Wilton; Enrico Picozza, Newtown, both of Conn.; Will Bloch, San Mateo, Calif.; Timothy M. Woudenberg, Bethel, Conn.

[73] Assignee: The Perkin-Elmer Corporation, Norwalk, Conn.

[21] Appl. No.: 823,735

[22] Filed: Mar. 25, 1997

Related U.S. Application Data

[62] Division of Ser. No. 299,033, Aug. 31, 1994, Pat. No. 5,720,923, which is a continuation of Ser. No. 98,711, Jul. 28, 1993, abandoned.

[51] Int. Cl.[6] .......................... G01N 21/01; G01N 21/62; G01N 33/50; C12M 1/02
[52] U.S. Cl. ............................ 422/68.1; 422/50; 422/62; 422/63; 422/67; 422/69; 422/82.05; 435/6; 435/91.1; 435/91.2; 435/283.1; 435/286.1; 435/286.2; 435/286.5; 435/287.1; 435/287.2; 435/287.3; 435/289.1; 435/293.1; 935/77; 935/78
[58] Field of Search .............................. 435/6, 91.1, 91.2, 435/810, 283.1, 286.1, 286.2, 286.5, 287.1, 287.2, 287.3, 289.1, 293.1; 422/50, 68.1, 62, 63, 67, 69, 82.05; 935/77, 78

[56] References Cited

U.S. PATENT DOCUMENTS 5,176,203   1/1993   Larzul ........................................ 165/61

*Primary Examiner*—Ardin H. Marschel
*Attorney, Agent, or Firm*—David Aker

[57] ABSTRACT

Apparatus and method for performing a nucleic acid amplification reaction and preferably a polymerase chain reaction (PCR) in a reaction mixture in at least one capillary tube. Several different embodiments are disclosed. One embodiment cycles a sample through a capillary tube loop passing through two thermostatted fluid baths. Another embodiment has the capillary tube routed alternatingly between two heat exchangers to that the sample makes only one pass through the tube. Other embodiments maintain the heat exchangers stationary and translate the samples between them. Still further embodiments maintain the samples stationary and either automatically translate or rotate the heat exchangers past the samples contained within the capillary tubes to perform the thermal cycles necessary for the amplification reaction.

20 Claims, 16 Drawing Sheets

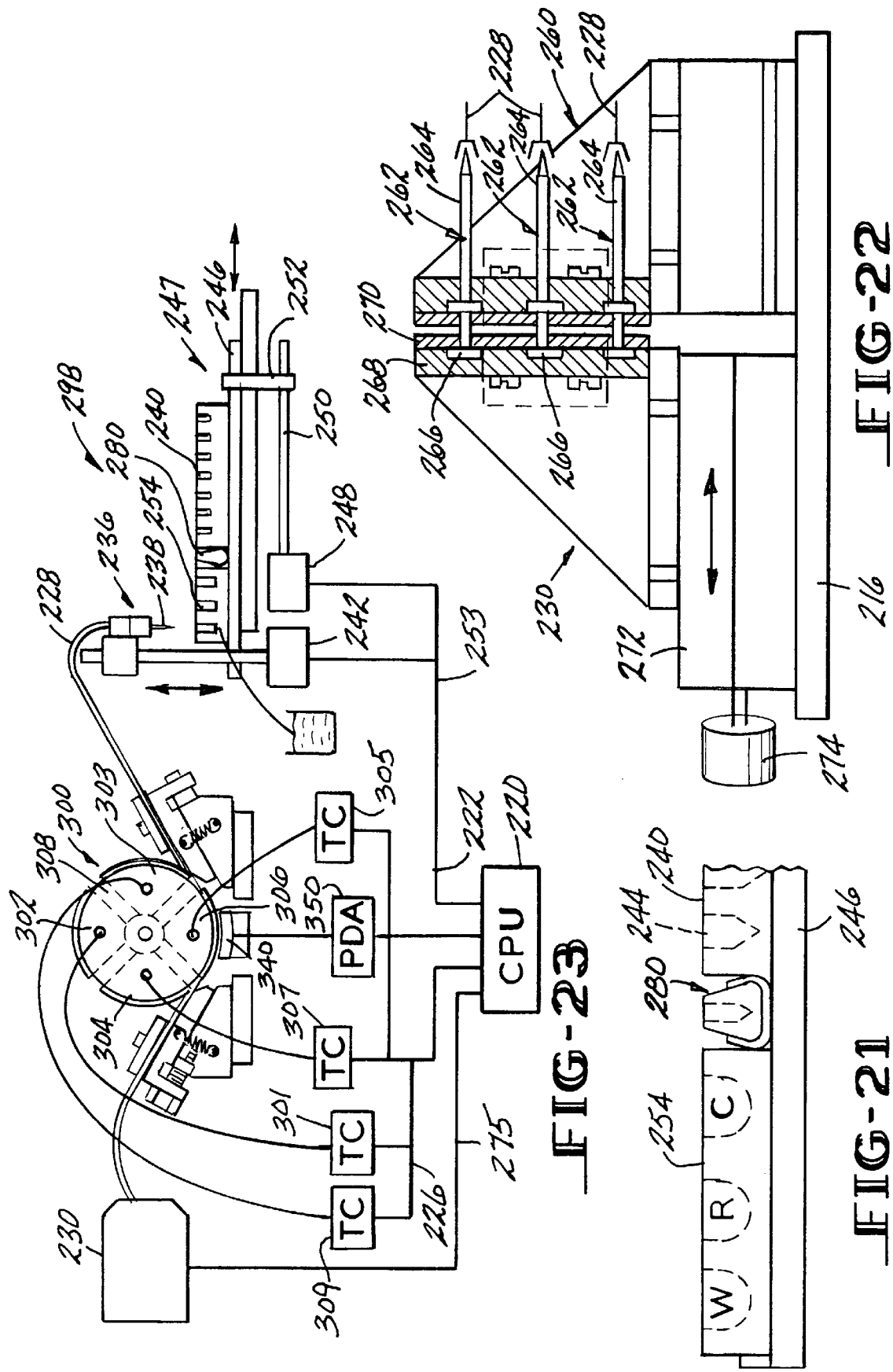

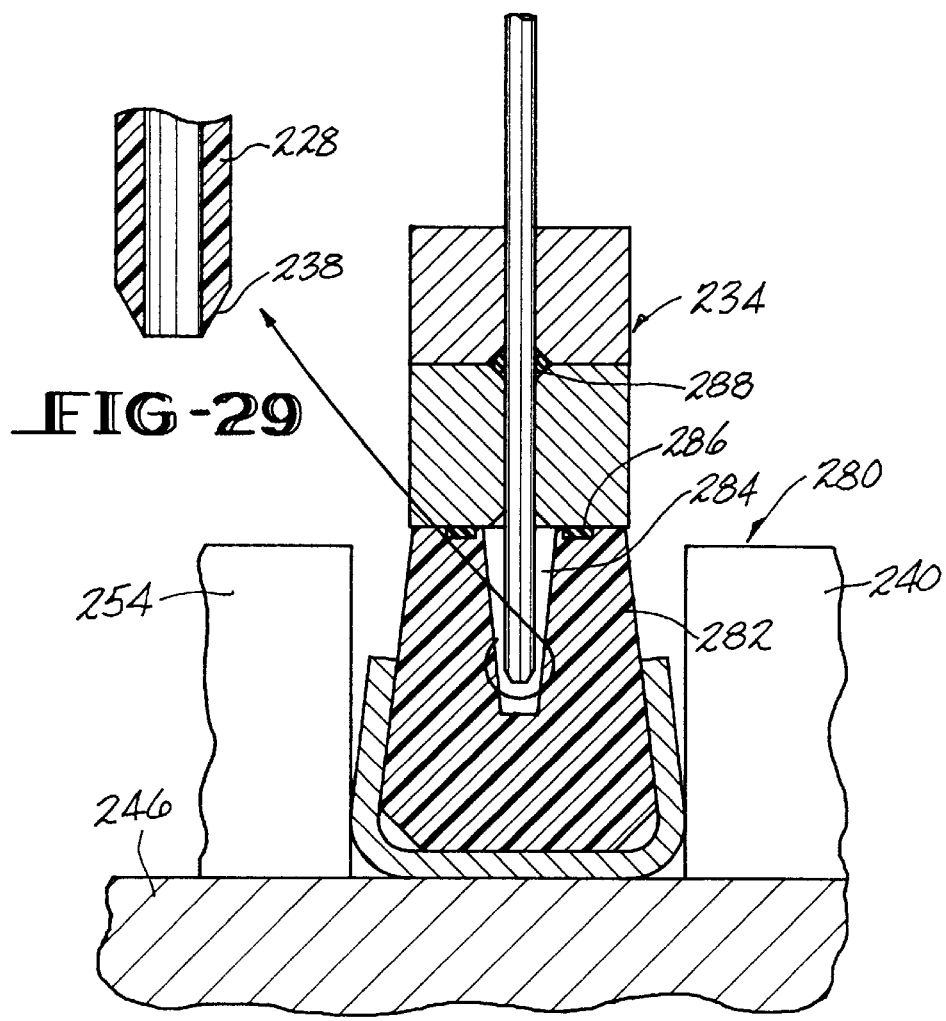
FIG-29
FIG-28
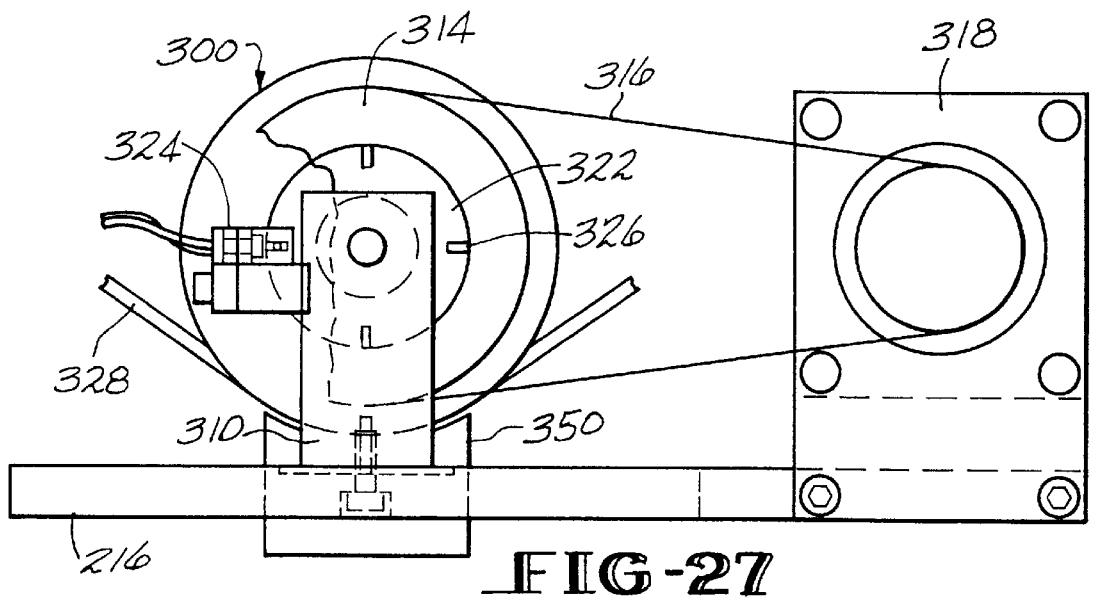
FIG-27

NUCLEIC ACID AMPLIFICATION REACTION APPARATUS

This is a divisional of application Ser. No. 08/299,033 filed on Aug. 31, 1994; now U.S. Pat. No. 5,720,923; which is a Continuation of Ser. No. 08/098,711 filed on Jul. 28, 1993, abandoned.

BACKGROUND OF THE INVENTION

1. Field of the Invention

This invention relates to amplifying nucleic acids by thermal cycling and, more particularly, to automated machines for performing amplification reactions such as a polymerase chain reaction (PCR).

2. Description of the Related Art

DNA (Deoxyribonucleic acid) may be amplified by thermally cycling a specially constituted liquid reaction mixture according to protocol such as a polymerase chain reaction (PCR) protocol which includes several incubations at different temperatures. The reaction mixture is comprised of various components such as the DNA to be amplified (the target) and at least two oligonucleotide primers selected in a predetermined way so as to be complementary to a portion of the target DNA. The reaction mixture also includes various buffers, enzymes, and deoxyribonucleotide triphosphates, such as DATP, dCTP, dGTP, and dTTP. The duplex DNA molecule is denatured into two complementary single strands. The primers then anneal to the strands, and, in PCR, nucleoside monophosphate residues are then linked to the primers in the presence of an enzyme such as a thermostable DNA polymerase to create a primer extension product. After primer extension, twice as many duplex DNA molecules exist. This process is repeated, each time approximately doubling the amount of DNA present. The result is an exponential increase in the concentration of target DNA, known as "amplification" of the target DNA.

The polymerase chain reaction (PCR) has proven to be a phenomenal success for genetic analysis, largely because it is simple and very versatile, and requires relatively low cost instrumentation. A key to this success is the concept of thermal cycling: alternating steps of melting DNA, annealing short primers to the resulting single strands, and extending those primers to make new copies of the double stranded DNA.

The methodology of the polymerase chain reaction is more fully described in U.S. Pat. Nos. 4,683,202 and 4,683,195 which are hereby incorporated by reference.

The polymerase chain reaction (hereafter PCR) has been performed in disposable reaction tubes such as small, plastic microcentrifuge tubes or test tubes which are placed in an instrument containing a thermally controlled heat exchanger. Examples of these instruments are disclosed in U.S. Pat. No. 5,038,852, U.S. application Ser. No. 07/709,374, filed Jun. 3, 1991, and U.S. application Ser. No. 07/871,264, filed Apr. 20, 1992, all of which are hereby incorporated by reference in their entirety.

The heat exchanger in these instruments is typically a metal block; however, hot air ovens and water baths also have been used. The temperature of the reaction mixture in the reaction tubes is changed in a cyclical fashion to cause denaturation, annealing and extension reactions to occur in the mixture. Three separate incubation temperatures commonly were used in the first generation PCR thermal cycling applications. These were typically around 94° C. for denaturation, around 55° C. for annealing, and around 72° C. for extension. More recently, the annealing and extension incubations have frequently been combined to yield a two temperature incubation process, typically around 94° C. for denaturation, and around 50°–65° C. for an annealing and extension incubation. The optimal incubation temperatures and times differ, however, with different targets.

Rapid, small scale, PCR capillary tube instruments also have appeared. For example, Idaho Technology introduced an instrument wherein the reaction mixture is placed in capillary tubes which are then sealed and placed in a hot air oven which cycles the temperature of the reaction mixtures in the tubes. A similar system was described in a paper by Wittwer et al., "Minimizing the Time Required for DNA Amplification by Efficient Heat Transfer to Small Samples", *Analytical Biochemistry* 186, 328–331 (1990). There, 100 microliter samples placed in thin capillary tubes were placed in an oven with a heating coil, a solenoid activated door and a fan. Air was used as the heat transfer medium. A very similar system was also described by Wittwer et al in another paper entitled "Automated Polymerase Chain Reaction in Capillary Tubes with Hot Air," *Nucleic Acids Research*, Volume 17, Number 11, pp. 4353–57 (1989).

The PCR volume has been limited to a range of from about 10 microliters to 1.5 milliliters in conventional heat block or liquid bath heat exchanger PCR instrument designs where the reaction mixture has been stored in microcentrifuge tubes. It is hard to scale up these volumes. The difficulty resides in the fixed dimensions of the wells in the heat exchange block for the tubes and the escalating difficulty in achieving heat transfer uniformity among all wells as dimensions get larger and heat gradient problems become more pronounced. As the volume of prior art reaction vessels is increased, the surface/volume ratio decreases. This change reduces the ability to change quickly the temperature of the reaction mixture in each tube because most heat exchange occurs between the walls of the tubes and the walls of the wells in the sample block.

In prior art instruments, thermal ramps were long because there was substantial lag in the temperature of the sample relative to the block caused by poor convection and conduction. Substantial thermal ramp durations between incubation temperatures were often necessary to prevent significant temperature gradients from developing because of the large thermal mass of the metal blocks used in many instruments as well as nondiffuse heat sources and sinks. These temperature gradients can cause non-uniform amplifications in different samples located at diverse points along the temperature gradient. There is no chemical or biological reason for using temperature ramps.

A capillary tube PCR instrument has the advantage of rapid thermal incubation transitions because the reaction volume and sample containment thicknesses can be minimized. One such instrument is disclosed in U.S. Pat. No. 5,176,203, issued to D. M. Larzul. The Larzul patent discloses a wheel shaped apparatus for automatic thermal cycling of a fluid sample contained in a closed loop or spiral coil of continuous capillary tube. Each loop of the tube is routed through three thermostatted zones. The sample is pushed through the loops by a motorized magnetic system in which a magnet on the end of a rotating central arm magnetically pulls a slug of mineral oil containing suspended metallic particles through the capillary tube. Since the slug abuts the sample in the capillary tube, the slug pushes the sample through the loop. The motorized system may be micro-processor controlled to regulate the movement of the sample in accordance with a predetermined protocol.

SUMMARY OF THE INVENTION

A number of alternative embodiments of capillary tube PCR instruments are envisioned herein which share certain common advantages. All of the instruments disclosed herein use thin walled capillary tubes to hold the reaction mixture as opposed to microcentrifuge tubes. A capillary tube as used herein is a tube which has an internal diameter less than 3 mm and preferably on the order of about 1 mm to 2 mm in internal diameter. These capillary tubes are heated and cooled in the embodiments taught herein according to a user-defined PCR protocol required of a particular reaction mixture fed into a programmable computer which, in turn, automatically controls sample handling, flow, velocity, pressure, and temperature to implement the protocol via conventional control programming. The differences among the various embodiments of the invention arise out of the different means used to heat and cool the PCR reaction mixture and different tube and fluid handling means used to move the reaction mixture.

For example, a first embodiment of the invention automatically pumps the reaction mixture repetitively through a continuous loop of capillary tube which is routed through two different thermostatted fluid baths, one at a denaturation temperature and one at an anneal/extend temperature. Additional baths could be added to increase the number of incubation temperatures.

A second embodiment directs the reaction mixture through a capillary tube only once, i.e. in a single pass. The capillary tube is routed in an alternating fashion back and forth between a first thermostatted heat exchanger held at a denaturation temperature and a second heat exchanger held at an anneal/extend temperature. Alternatively, a third heat exchanger may also be used if the anneal and extend temperatures differ. A positive displacement or peristaltic pump or syringe is used to push the reaction mixture through the single pass tube out into a product collection vessel.

A third embodiment of the invention involves a stationary reaction mixture in a multiple fluid bath arrangement. This embodiment uses a single loop of capillary tube for each sample. The portions of the loops containing the samples are enclosed in a reaction chamber. A hot fluid at a denaturation temperature is pumped into this reaction chamber from a first thermostatted fluid bath and held there during the denaturation incubation. Fluid at an anneal/extend temperature is pumped into the chamber from a second temperature stable bath after removal of the hot fluid from the first temperature stable bath to implement the anneal/extend incubation. This process is repeated as necessary to complete the PCR protocol.

A fourth embodiment utilizes two or three temperature stable fluid baths, each of which is constantly circulating its fluid through a separate conduit. Each fluid stream is thermostatted at one of the necessary PCR incubation temperatures. A single cylindrical heat exchanger chamber with a wire mesh at the input end is connected through a valve system to the fluid streams. The wire mesh holds individual small capillary tube reaction mixture vessels, which are each sealed at both ends in place in the heat exchange chamber. The vessels are held in a spaced relationship or array by the mesh because the seal at one end of each capillary tube vessel is too large to fit through the mesh. The valve system, preferably under the control of a computer or other automated controller, is used to select one of the streams at a time to be routed through the cylindrical heat exchanger chamber while the other one or two streams are bypassed around it. For example, to carry out a denaturation incubation, a stream of 94° C. fluid is routed through the heat exchanger chamber while an anneal stream at 55° C. and an extend stream at 75° C. are routed around the heat exchange chamber.

A fifth embodiment uses two metal blocks each of which has its temperature stabilized at one of two temperatures needed for the denaturation and anneal/extend incubations. An open-ended, thin-walled capillary tube is routed through and between these two metal blocks. A peristaltic pump or a plunger and seal arrangement, similar to a syringe, is connected to one end of the capillary tube, under control of a computer programmed to carry out the PCR protocol. The pump or plunger is activated back and forth to draw reaction mixture into the capillary tube, move it into the region surrounded by the denaturation block, i.e., the block held at the denaturation temperature, and then move the reaction mixture through the capillary tube into the region of the capillary tube surrounded by the block held at the anneal/extend temperature. This cycle is repeated the required number of times to complete the PCR protocol. The plunger is then moved to discharge the PCR product. Alternatively, the blocks themselves could be translated back and forth against a stationary capillary tube containing the mixture to thermally cycle the mixture.

A sixth embodiment of the capillary PCR instrument in accordance with the invention is somewhat similar to the fifth in that spaced metal heat exchanger blocks are used. This embodiment preferably has a pair of spaced heat exchanger blocks, a plurality of open-ended capillary tubes routed through each of the blocks, and an automated sample handling system. This handling system simultaneously inserts the end of each of the capillary tubes into reaction mixture containers, withdraws the reaction mixture into the capillary tubes, then translates the mixture between the heat exchanger blocks, and discharges the final PCR product from the capillary tubes into suitable containers, all under computer control. In addition, the handling system performs capillary tube cleansing, rinsing, and sample tray translation and elevation functions, all under computer control so that a tray of 48 or 96 samples can be thermally cycled automatically in groups, if necessary, e.g. 12 at a time.

A seventh embodiment of the invention is designed to move the heat source rather than the sample. This embodiment has a moving thermal heat exchanger and preferably has a cylindrical heat exchange thermal platen or drum, divided into two, three, four, or more axially extending radial segments. Each segment is thermostatically controlled at an appropriate incubation temperature for denaturation, extension, or annealing. If only two incubation temperatures are required and three segments are provided, the third segment may be used to accelerate the transition from the anneal/extension temperature to the denaturation temperature. Similarly, if four segments are provided, and two incubation temperatures are required, then the other two segments may be used to accelerate the transitions in both directions between the anneal/extension temperature and the denaturation temperature.

The arcuate outer surface of each of the segments has a plurality of parallel grooves, each aligned to receive a capillary tube. The capillary tubes are routed so that there is preferably full tube contact along the groove length of one segment. A handling system is also included as in the sixth embodiment. A peristaltic pump or syringe type plunger and seal assembly is used to draw the reaction mixture into each of the capillary tubes to a position adjacent to the contacting cylindrical heat exchange segment. The PCR protocol is then performed by rotating the cylindrical heat-exchange platen between alternate angular positions in which each segment is preferably in full contact with the capillary tubes for the required incubation period.

All of the instruments described herein are preferably controlled by computers which are user-programmable, such as a personal computer (PC) or an internal microprocessor based controller of conventional design, adapted to receive data defining the desired PCR protocol and to carry out the protocol by issuing the proper control signals to operate the necessary pumps and valve switches, and/or generate the heat exchanger medium movements needed to cause the reaction mixture to be heated and cooled.

All of the instruments described herein enjoy the advantage of not needing to change the temperature of a large thermal mass in order to cycle the reaction mixture between the anneal/extend incubation temperature(s) and the denaturation temperature. This simplification reduces thermal gradient problems and simplifies the thermal design of the instruments such that plural reaction mixtures can all be subjected to the same PCR incubations at the same time without variance caused by nonuniformities in the instrument itself.

The primary portions of the instruments of the present invention which undergo substantive thermal transients are the capillary tube walls. Because of the low thermal mass and high thermal conductivity of these portions of the instruments, very rapid thermal cycling of samples can be carried out. Use of capillary tubes in most of the instruments described herein also permits simple scaling of the amount of finished product without the need for heat exchanger redesign to minimize nonuniformities in temperature among plural samples being processed.

The capillary tube PCR instruments disclosed herein enjoy the advantage generally of being capable of very rapid temperature changes for the reasons described above. This improvement shortens the overall time for a PCR cycle and considerably shortens the overall time for a complete amplification protocol. These and other objects, features, and advantages of the invention will become more apparent from a reading of the following detailed description when taken in conjunction with the drawing and appended claims.

BRIEF DESCRIPTION OF THE DRAWINGS

FIG. 21 is an enlarged partial side view of the sample translation assembly in the apparatus shown in FIG. 20.

FIG. 22 is an enlarged side view of the sample transfer device in the apparatus shown in FIG. 20.

FIG. 23 is a simplified side view of a seventh embodiment of a capillary PCR apparatus having a rotating drum thermal heat exchanger for an array of capillary reaction tubes in accordance with the invention.

FIG. 27 is an enlarged partial rear view of the heat exchanger assembly shown in FIG. 24 in accordance with the invention.

FIG. 28 is a partial sectional view of the sample handling assembly shown in FIGS. 20 and 24.

FIG. 29 is an enlarged sectional view of the tip of a capillary tube shown in FIG. 28.

DETAILED DESCRIPTION OF THE PREFERRED EMBODIMENTS

Continuous Loop Capillary Thermal Cycler

Figure 1:
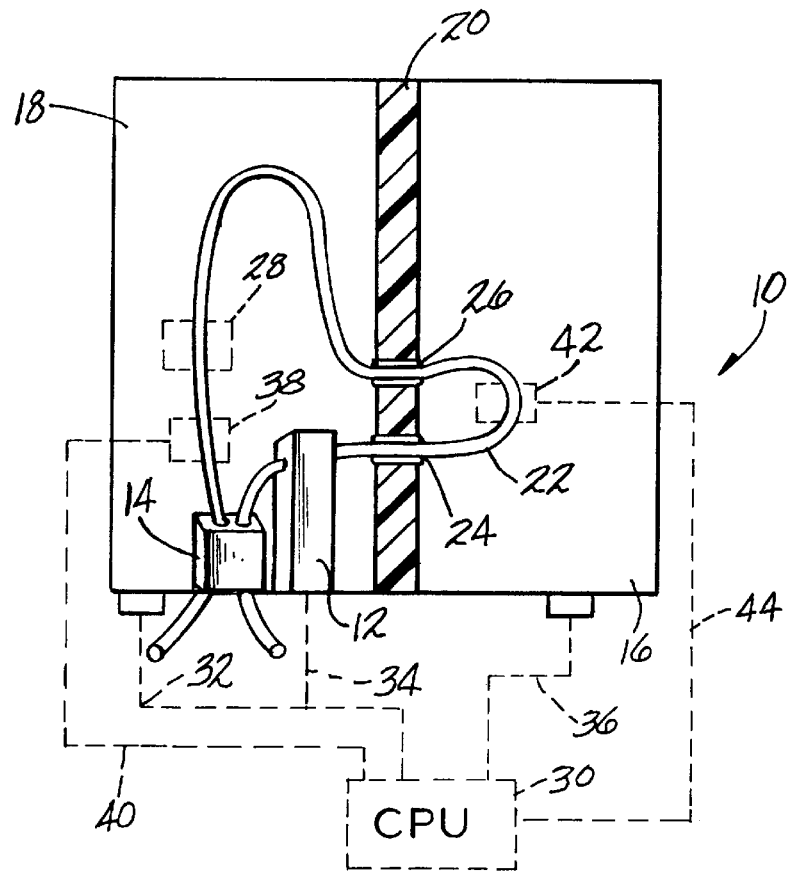
FIG. 1 is a block diagram of a capillary tube PCR thermal cycler instrument in accordance with a first embodiment of the present invention.

Referring to FIG. 1, there is shown a first embodiment of a capillary-tube PCR instrument in accordance with the invention. The instrument 10 comprises two different thermostable liquid baths with the reaction mixture pumped therebetween in a capillary-tube loop. This embodiment is capable of performing PCR on a reaction volume of any scale including greater than about 1 milliliter. Two reaction temperatures are used for the denaturation and annealing/extension incubations. Complete control over the incubation times at each temperature is provided by a pump 12 and the ratio of tube length in each bath.

Typical two-temperature PCR involves cycling a reaction mixture between about 60° C. and 95° C. with residence or incubation times in the range of 1–300 seconds. Three temperature stable liquid baths may be used for three separate incubation temperatures. Kim and Smithies published an article in Nucleic Acids Research 16, 8887–8903 which teaches that incubation at the intermediate "extension" temperature is unnecessary. Accordingly, the embodiment of FIG. 1 uses only two temperatures based upon this research, one in the range from 37°–72° C. for annealing and extension and one in the 85°–98° C. range for denaturation.

The first embodiment is designed for preparative scale PCR with volumes upward of about 1 milliliter with no set upper bound other than potentially the maximum volume of the reaction tube loop. The preferred target DNA segment may have between about 100–10,000 base pairs (bp). The first embodiment is designed for optimized consumption of the stoichiometrically limiting and most expensive reagents needed for the PCR reaction mixture, i.e., the two primers.

In FIG. 1, the high temperature bath is shown at 16 and the low temperature bath is shown at 18. These two baths are separated by a layer of insulation 20 which is selected to minimize the flow of heat between the two baths 16 and 18. Bath 16 is thermostatically controlled to a user-defined temperature preferably between 85° and 98° C.±0.1°–0.5° C. Bath 18 is thermostatically controlled at a user-defined temperature between 40° C. and 70° C., preferably within the same tolerance. Each bath may employ turbulent mixing via conventional means such as mixer blades, etc. to achieve thermal uniformity.

A reaction vessel 22 comprises a length of relatively thin-walled plastic capillary tubing which forms a loop which penetrates the walls between the two baths through two O-ring seals 24 and 26, submerged below the liquid levels. The inner diameter of the reaction tube 22 and its length establish the theoretical upper boundary for the reaction volume. Narrower tubing of greater length is preferred to achieve better temperature control.

A 4-way valve 14 is immersed in the liquid within the low temperature bath 18 and is used to alter the fluid flow path to introduce a reaction mixture sample into the reaction vessel 22 and remove finished PCR product. A peristaltic pump 12 also located in bath 18 is used to circulate the reaction mixture into, out of, and through the reaction vessel 22. The pump 12 has a closely controlled and calibrated flow rate. Peristaltic pumps are preferred so that the reaction mixture contacts only plastic.

If the tubing used in both baths has the same internal and external diameters, the residence time in each bath for the reaction mixture is controlled by the ratio of the tubing lengths in the two baths. Generally, it would be preferable to use denaturation incubation times in bath 16 of 5–15 seconds and annealing/extension incubation times of up to several minutes in bath 18. In this first embodiment, a single continuous reaction tube 22 passes between the two baths through leak proof O-ring seals 24, 26 and both ends connect to the 4-way valve 14. The use of O-ring seals 24, 26 through which the reaction tube can slide allows incubation times to be adjusted manually by pulling the tube through the O-rings to adjust the relative lengths of tube in each bath.

The 4-way valve has a position in which reaction product from the length of tube 22 in the low temperature bath 18 can be pumped back into the high temperature bath 16 to commence a new cycle, a position for discharge of PCR products at the completion of a PCR protocol, and a position where new reaction mixture can be introduced to the reaction tube 22 after suitable procedures are performed to flush, clean or, if necessary, replace the reaction tube 22.

An immersible, fiber-optic spectrophotometric detector 28 may be included, preferably having its sensor in the low temperature bath 18, to monitor the progress of the PCR reaction from one cycle to another. This spectrophotometric (UV) detector 28 detects the hypochromism expected as dNTPs are incorporated into the DNA product. Only a marginal differential signal will typically be seen until the later thermal cycles in the PCR protocol. A similar fluorescence detector may also be used in performance of various "Taqman" based assays.

Reaction tube 22 should be a loop of capillary tubing made of PCR-compatible material such as Polytetrafluoroethylene (PTFE), e.g. DuPont Teflon®, which has an inside diameter of less than 3 mm and is preferably between about 1 mm and 2 mm. The tubing should have a wall thickness between 0.2–0.5 mm and is preferably about 0.3 mm. The capillary size of the tube 22 minimizes the effects of the heat transfer gradient across the tube wall as the reaction mix passes through the bath. In addition, the small size permits the use of an air bubble or an immiscible fluid such as an oil to be used as a discontinuity to demark the ends of the reaction mixture sample volume and as a pusher to drive the reaction mix predictably through the baths 16 and 18 via the peristaltic pump 12 and through the 4-way valve 14.

The bubble or other fluid discontinuity travelling through the reaction tube 22 can be used to provide a simple, automatable cycle counter through use of suitable apparatus to detect the passage of the fluid discontinuity. Suitable apparatus to detect the passage of the discontinuity would include a photoelectric or capacitance sensor 42 mounted on the tube 22, again, in both.

Operation of the first embodiment is simple. After the reaction mixture is introduced through the 4-way valve 14 into the tube 22, it is continuously pumped through the thermostatted baths 16 and 18 with a total cycle time defined by the speed of the pump 12 and the tubing volume. Each passage of the mixture through the complete loop is one complete PCR cycle. The entire reaction volume may not be at a single temperature at any one time, but each volume element of the reaction mixture experiences approximately a uniform residence time at each temperature. Because of the relatively narrow tubing bore and surface roughness, there will be some turbulent mixing within the mixture segment as it passes through the tubing. This mixing enhances the sharpness of the thermal control. After the desired number of cycles have been completed, the finished PCR product is pumped out through the 4-way valve.

Commercially available thermostatted baths can regulate the bath temperature within 0.1° C., thereby offering precise temperature control. No special flow controls or software are needed in this embodiment since peristaltic pumps with very precise flow rates are also commercially available.

It may be desirable to automatically alter the annealing/extension incubation temperature or time late in the PCR protocol after large amounts of finished product have begun to build up in the reaction tube 22. Automated or manual changes in the pump flow rate or the lower bath temperature setpoint may be implemented through a suitably programmed CPU 30 coupled to a pump speed control input and a bath temperature control input through a suitable interface. It may also be desirable to gradually increase the denaturation temperature over the complete duration of an amplification, in a manner that is linear with total elapsed time. This protocol may be accomplished through a suitably programmed CPU coupled to a temperature control input of the high temperature bath 16 and to a cycle counter. Such a control scheme is symbolized schematically by the CPU 30 shown in FIG. 1 in dashed lines with control lines 32, 34, and 36 coupled to the low temperature bath 18, the peristaltic pump 12, and the high temperature bath 16, respectively.

It may also be desirable to accommodate supplemental reagent additions such as dNTPs, enzyme or primers throughout the PCR protocol or in the later cycles in some alternative embodiments. This may be done automatically under the control of CPU 30 via a reagent addition valving mechanism symbolized schematically by block 38 controlled via signals on control bus 40. Various embodiments of the valving mechanism 38 may provide for continuous addition of reagents or addition only in later cycles. The CPU 30 is coupled to a cycle counter 42 via a control bus 44 in embodiments where the number of cycles completed needs to be monitored, such as embodiments where reagents are to be added at specific points later in the PCR protocol. Reagent additions later in the protocol can maximize the total yield. For example, fidelity can be improved by keeping the dNTP concentrations in the 10–50 micromolar range, but these levels might prove to be stoichiometrically limiting in later cycles. Therefore, an order-of-magnitude jump in Mg-dNTP concentration late in the amplification protocol may improve yield dramatically with little net effect on fidelity. Similarly, primer concentration may be increased in late cycles to boost total yield. This embellishment would improve product purity as well.

The inside surface of the capillary tubing creates drag on the portion of the sample liquid adjacent the tube wall. An air bubble or other fluid discontinuity is useful between each sample to push the entire sample as a unit along the capillary flow path. Otherwise a parabolic flow profile would exist across the capillary. Use of an air bubble between samples or between sample segments results in "slug" flow wherein sample "slugs" are pushed through the capillary tubes.

Single-Pass Capillary Thermal Cycler

Figure 2:
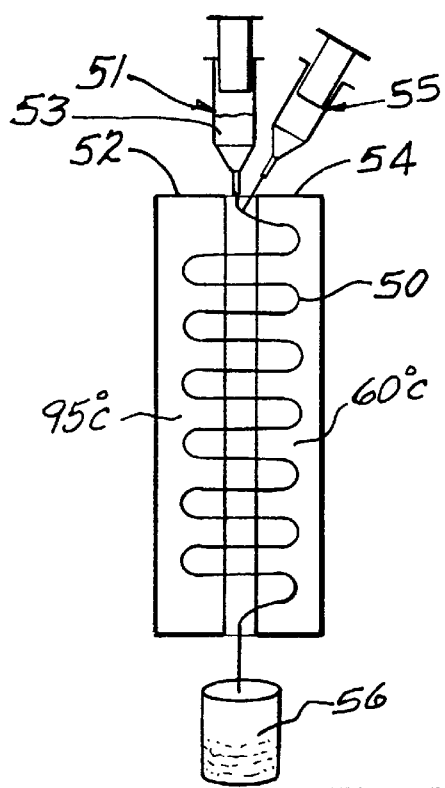
FIG. 2 is a block diagram of a capillary tube PCR instrument in accordance with a second embodiment of the present invention.

A simplified schematic diagram of a second embodiment of a capillary tube PCR instrument for performing PCR in comparatively large volumes is shown in FIG. 2. This embodiment uses a length of capillary tubing 50 that is routed in and out of hot and cold sources of the appropriate temperature a number of times. The embodiment of FIG. 2 uses a reaction chamber in the form of series loops of capillary tubing 50. Each loop has a portion which passes through an equilibrated hot zone 52 and a portion which passes through an equilibrated cool zone 54. Typically, the hot zone 52 is a liquid bath wherein the liquid is controlled to have a constant temperature in the range of temperatures needed to perform denaturation in PCR processes, typically around 95° C. Likewise, the cool zone is usually a liquid bath with liquid therein having its temperature controlled so as to maintain a constant temperature in the range of temperatures needed for annealing and extension, typically around 60° C.

Other temperatures could be used within the denaturation and anneal/extend ranges, and each of the hot and cool zones 52, 54 could be temperature controlled solid blocks through which the tubing 50 passes, such as a metal block. Also, a hot gas oven could be used for denaturation and a cool gas oven used for the cool zone. The preferred structure for the hot and cool temperature controlled zones, however, is either two temperature-controlled metal blocks or two temperature-controlled water baths. The length of the tubing 50, its internal diameter, the length of tubing in each of the hot and cool zones, and the flow rate of reaction mixture inside the tube are all factors in the control of the amplification.

In the second embodiment of FIG. 2, the motive force for moving the PCR reaction mixture along the tubing 50 is a sterile, disposable syringe 51 capable of holding large volumes of reaction mixture 53. The syringe 51 is loaded with the reaction mixture components well known to those skilled in the art, and the sample nucleic acid to be amplified. The syringe 51 is then operated by hand, compressed gas, or using a syringe pump to move the reaction mixture 53 into and through the tubing 50.

Another syringe 55 containing air or an immiscible fluid such as mineral oil may be connected in parallel with the syringe 55 to the tubing 50. The syringe 55 is operated intermittently to inject air bubbles or immiscible fluid bubbles into the flow stream of reagent mixture 53 in the tubing 50. This will ensure that slug flow dominates throughout the flow path so that each volume element of the reaction mixture 53 experiences the same number and duration of thermal incubations. The use of air to cause slug flow to occur is preferred as, upon fluid exit, only the finished PCR product is collected in the container 56. The use of the syringe 55 may not be required for preparative-scale PCR; as long as enough cycles are run to exhaust the concentration of primers and as long as the dynamic residence time within each zone is sufficient to cause most of the sample to reach incubation temperature. The syringe 55 may also be used to introduce a missing reagent to effect a "hot start".

The length of the tubing 50 in each zone is chosen so that each time a unit of volume of the reaction mixture has passed once through the hot zone and once through the cool zone, one complete PCR cycle will have been completed. The number of loops in the system determines the number of cycles performed. The preferred method of operation includes leaving an air pocket at the top of the syringe 51 to force all the amplified product out of and completely through the tubing.

The tubing of the reaction tube 50 may be either glass (coated with an appropriate silanizing agent), metal, or plastic of a type which will not interfere with the PCR process. Preferably, the tubing is of the single-use, disposable variety. Plastic, polypropylene or teflon is preferred. However, metal tubing, coated with parylene, may be preferred in this embodiment because it has better heat conductance, it holds its shape after being bent, the internal diameter of the tubing can be smaller so as to provide more turbulent mixing during slug flow, and metal is more thermally compatible with a heated block than is plastic tubing.

The principal advantage of the second embodiment shown in FIG. 2 is the large volume of amplified product that can be obtained in one pass. It would be more convenient to operate than the conventional type of PCR instrument wherein many individual 100 microliter reaction mixes must be prepared to obtain a large volume of amplified product. The individual reaction mixtures conventionally must be prepared, amplified, pooled, and realiquoted, which is a tedious and time-consuming procedure.

Multiple Water Bath Capillary Thermal Cycler

Figure 3:
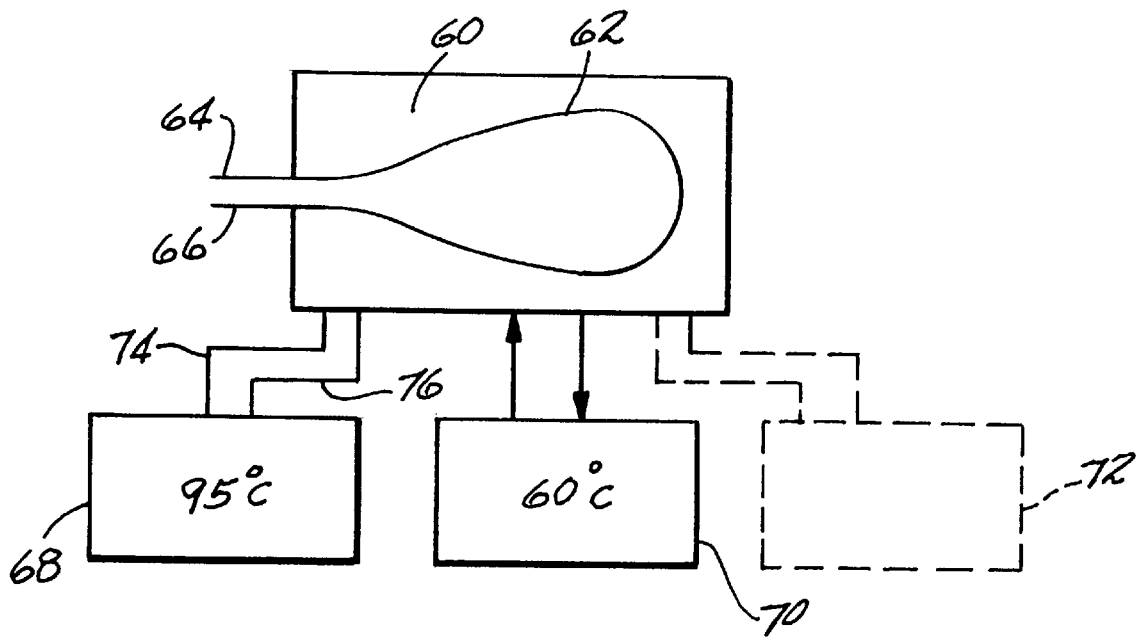
FIG. 3 is a block diagram of a capillary tube PCR instrument in accordance with a third embodiment of the invention for performing small scale, very rapid PCR.

A diagram of a third embodiment of a capillary tube PCR instrument in accordance with the invention for performing relatively small-scale, very rapid PCR using water baths to change the temperature of a chamber in which the capillary tube resides is shown in FIG. 3. In this instrument, a liquid tight chamber 60 contains at least one capillary tube reaction chamber 62 which has both ends 64 and 66 protruding from the chamber through liquid-tight grommets. As is the case for all the capillary tube instruments disclosed herein, the capillary tube 62 may be made of metal, preferably parylene coated, or plastic, with Teflon or polypropylene preferred for the plastic embodiments. From 1 to 25 microliters of the PCR reaction mixture is injected into the portion of the capillary tube 62 in the chamber 60 by any suitable means.

The chamber 60 is in fluid communication with either two or three temperature controlled fluid baths. In FIG. 3, only two baths are shown: a high-temperature bath 68 kept at a constant temperature in the denaturation temperature range such as 95° C.; and a cooler bath 70 kept at a constant temperature in the annealing/extension range such as 60° C. Embodiments where three separate incubations for denaturation, annealing, and extension processes are desired require a third temperature-controlled fluid bath 72 indicated by the dashed lines in FIG. 3.

Each fluid bath may have its own integral fluid pump coupled to input and output pipes such as pipes 74 and 76, respectively, for bath 68. In these embodiments, suitable control circuitry (not shown) is used to pump hot fluid from bath 68 into chamber 60 to a sufficient level to fully immerse the capillary tube 62 for a predetermined period of time for the denaturation process to occur, typically from 1 second to 3 minutes. Water flow into and out of the chamber is typically set at at least one liter per minute to make switches between temperatures faster.

After completion of the denaturation incubation, suitable control signals are issued to cause the 95° C. fluid in the chamber 60 to be pumped back into the hot fluid bath 68, and, when the level of fluid in the chamber 60 is sufficiently low, suitable control signals are issued to cause the cooler fluid from the bath 70 to be pumped into the chamber 60. A liquid level sensor mechanism such as a float switch (not shown) can be used to determine when to switch on the pump in the reservoir 70 to begin filling the chamber 60 with fluid of a temperature to carry out an anneal/extend incubation. The reaction mixture changes temperature rapidly when the chamber 60 is filled with a different-temperature fluid because capillary tube is used which constitutes a small thermal mass. In this third embodiment, the fluid from each water bath 68, 70, or 72 may be pumped back into its original bath 68, 70, 72 when the incubation at that temperature is over. However, this procedure leaves the capillary tube 62 temporarily suspended in air before the fluid from the next bath enters the chamber 60. The relative volumes of the chamber 60 and the water baths are such that the volume of the chamber 60 is tiny compared to the volume of the water baths. Therefore it is preferable to route the fluid from the chamber 60 to the water bath which is providing the new fluid for the next incubation without prior drainage of chamber 60. In other words, fluid may be simply transferred through the lines between each bath and the chamber for each incubation. Even though the temperature of the fluid from the chamber 60 is different from the temperature of the fluid in the fluid bath being pumped in for the new incubation, the thermal mass of the water baths is so large that there is no significant change in the bath temperature, and the bath controls can maintain constant bath temperatures. This design permits temperature changes to be accomplished typically in less than 1 second.

Figure 4:
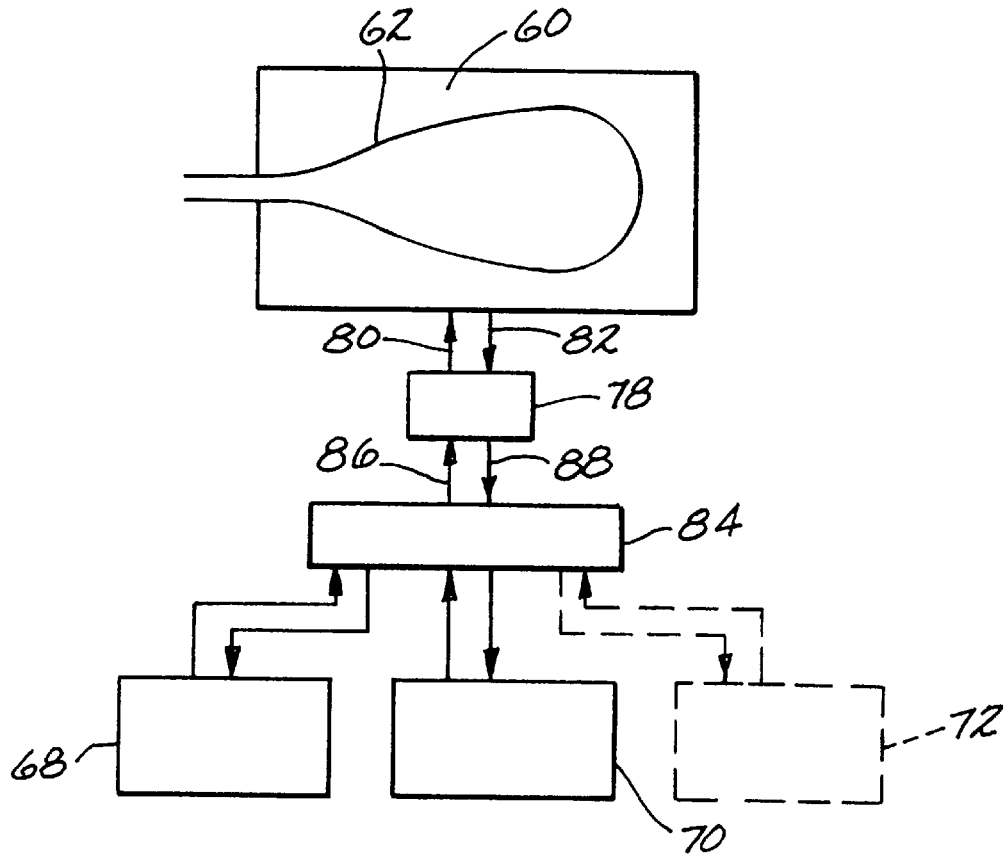
FIG. 4 is a block diagram of a capillary tube instrument in accordance with an alternative third embodiment of the invention.

FIG. 4 represents an alternative third embodiment of a capillary-tube PCR instrument similar to the third embodiment shown in FIG. 3, using a single pump to pump the fluid from any of the baths. Like-numbered elements in FIGS. 3 and 4 mean that the structures are the same and that they perform the same function. In FIG. 4, a single bi-directional pump 78 is coupled to the chamber 60 by input pipe 80 and output pipe 82. This pump is also coupled to the output port of a fluid multiplexer 84 by input pipe 86 and output pipe 88. The fluid multiplexer 84 has a plurality of input ports, each of which is coupled to one of the two or three temperature-controlled baths 68, 70, and 72. Each input port is coupled to its corresponding fluid bath by two pipes such as input pipe 86 and output pipe 88 for fluid bath 68.

The fluid multiplexer 84 and pump 78 are controlled by a suitable conventional programmable controller (not shown) with suitable interface circuitry to carry out the appropriate position selection of one of the fluid flow input ports for coupling to the fluid flow output port and appropriate switching of direction of pumping by the pump 78 so as to carry out the desired PCR protocol of sequential incubations.

The instruments shown in FIGS. 3 and 4 can perform PCR amplification on volumes under 10 microliters without using an oil or other fluid discontinuity means because the mixture is stationary during the PCR protocol. The instruments shown in FIGS. 3 and 4 can also perform PCR incubation steps in as little time as 1 second, and total time for a two-incubation PCR protocol cycle can be reduced to as little as 8 seconds by the use of 1 second denaturation and anneal/extend times of from 7–30 seconds. When anneal/extend intervals are this short, however, large concentrations of thermostable enzyme such as Taq polymerase may be required in the sample volume.

Constant Circulating Fluid Bath Capillary Thermal Cycler

Figure 5:
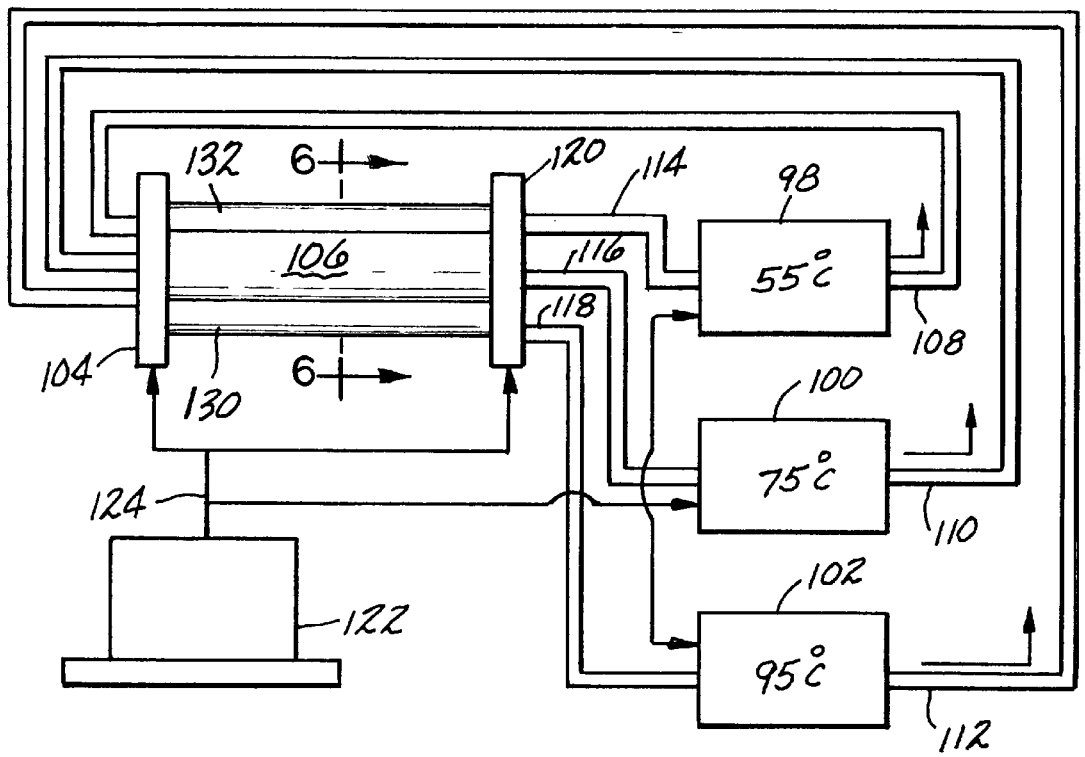
FIG. 5 is a block diagram of a capillary tube PCR apparatus in accordance with a fourth embodiment of the invention using three thermostatted circulating fluid baths and a single reaction chamber.

A fourth embodiment of the capillary tube PCR instrument of the invention is shown in FIG. 5. This illustrated embodiment has three thermostatted fluid baths and a single reaction chamber which contains sealed capillary tubes holding the reaction mixture samples. If only two temperatures are needed for the PCR protocol, however, the third bath can be eliminated. The third bath is described herein for completeness.

A first bath 98 maintains a body of fluid at some temperature in the range of annealing temperatures such as 55° C. A second bath 100 maintains the temperature of fluid contained therein at a temperature in the range of temperatures effective for the extension incubation, for example 75° C. A third bath 102 maintains the temperature of fluid contained therein at a temperature in the range of temperatures effective for denaturation, typically 95° C. Each fluid bath has a pump therein which can pump the fluid in the bath out an output pipe 108, through a valve mechanism 104 at the input side of a reaction chamber 106. Similarly, the output pipe 110 of bath 100 and the output pipe 112 of bath 102 connects to valve mechanism 104. Fluid from reaction chamber 106 returns to its bath through an output valve mechanism 120 and each bath includes a return pipe, i.e., pipes 114, 116, and 118 for baths 98, 100, and 102, respectively.

A computer 122 is coupled via a control bus 124 to the pumps of the various baths to control the fluid flow rate in the preferred embodiment. Constant flow rates may also be used in alternative embodiments, in which case coupling of the pumps to the computer 122 may not be necessary as the pumps will be running continuously at the same flow rate.

The computer 122 is also coupled to the input valve mechanism 104 and the output valve mechanism 120. The purpose of the computer control of the valve mechanisms is to selectively direct the flow of one temperature fluid into the reaction chamber 106 and bypass the other flows in accordance with data stored in the computer 122 defining the desired PCR protocol.

As with other PCR instruments such as is described in U.S. Ser. No. 07/871,264, filed Apr. 20, 1992, the PCR protocol may be defined by checkpoint data defining the temperature and duration of all the required PCR incubations, the number of cycles to perform, and linking data to any other desired protocols to run upon completion of any given protocol. The data defining the desired protocol may be entered by the user or it may be a predefined program.

The PCR protocol is implemented by the computer 122 by controlling the input valve mechanism 104 such that only one flow from one of the baths is directed through the reaction chamber at any particular time, and all the other flows are bypassed through alternate pathways that do not pass through the reaction chamber 106. Valve mechanism 104 may be a cylindrical or rotary solenoid-operated or air-operated multiport valve well known to those skilled in the art. The flow sequence is better understood by reference to FIGS. 6–9 which shows one arrangement of the reaction chamber 106 and the alternate flow paths in various states of bypass.

The tubular reaction chamber 106 preferably has the bypass piping from the two or three baths 98, 100, and 102, also tubular, mounted around the outside of the chamber 106. Valve mechanisms 104 and 120 are at opposite ends of chamber 106. A transverse sectional view through this arrangement would show the interior of chamber 106 surrounded by the bypass piping. This sectional view is schematically illustrated in FIGS. 6 through 9.

It is to be understood that if the anneal and extension temperatures are the same, then only two baths and bypass paths would be necessary and the instrument in FIGS. 5 through 9 would required only two rather than three bypass paths.

Figures 6, 7, 8, 9:
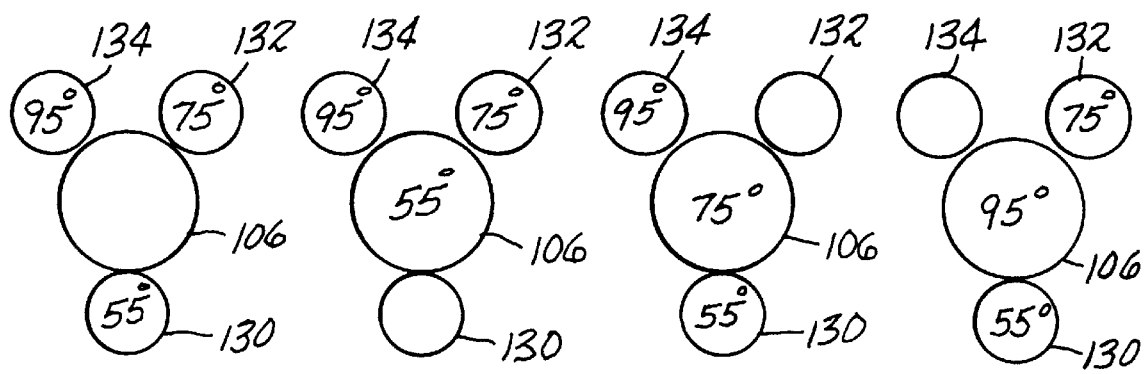
FIG. 6 is a simplified sectional view of the reaction chamber of the apparatus shown in FIG. 5 taken along the line 6—6 with all flows bypassed.
FIG. 7 is a simplified sectional of the reaction chamber of the apparatus as in FIG. 6 with the 55° C. flow directed through the reaction chamber and all other flows bypassed.
FIG. 8 is a simplified sectional of the reaction chamber of the apparatus as in FIG. 6 with the 75° C. flow directed through the reaction chamber and all other flows bypassed.
FIG. 9 is a simplified sectional of the reaction chamber of the apparatus shown in FIG. 6 with the 95° C. flow directed through the reaction chamber and all other flows bypassed.

FIG. 6 shows the reaction chamber 106 empty, with all three flows bypassed through their alternate pathways. The anneal temperature fluid flows through bypass pathway 130, the extension temperature fluid flows through bypass pathway 132, and the denaturation temperature fluid flows through the bypass pathway 134.

FIG. 7 reflects the valve configuration for the anneal incubation. In this incubation, the 55° C. fluid from bath 98 is switched via computer 122 by solenoid-operated valves in valving mechanism 104 so as to pass through the reaction chamber 106. The temperature of the reaction mixtures in the capillary tubes in the reaction chamber is then rapidly equilibrated at 55° C. Both the 75° C. fluid from bath 100 and the 95° C. fluid from bath 102 remain connected to their bypass pathways 132 and 134, respectively.

After the appropriate annealing incubation interval has passed, the computer 122 activates the valve mechanisms 104 and 120 to switch the flows to the configuration shown in FIG. 8 to carry out the extension incubation. In this incubation, the 95° C. and 55° C. fluid flows are bypassed and the 75° C. flow is switched to pass through the reaction chamber 106.

Upon completion of the extension incubation, denaturation to split the double-stranded extension product into single stranded templates for the next cycle must be performed. The computer 122 again activates valves 104 and 120 to switch the flows to the configuration shown in FIG. 9. Here the 55° C. fluid flow and the 75° C. fluid flow are bypassed, and the 95° C. fluid flow is switched to pass through the reaction chamber 106. This step completes one PCR cycle. The computer 122 then typically repeats the cycle the desired number of times to complete the PCR protocol.

The reaction chamber 106 is a tubular chamber with a wire screen mesh transversely mounted in the reaction chamber at the input end. The reaction mixture is stored in thin-walled (0.01–0.03 mm) sections of seamless, inert, puncture-free plastic capillary tubing of various diameters depending upon the desired volume of finished product. Inside diameters up to 2 mm and as small as 0.075 mm are available. The tubing typically has a maximum continuous service temperature rating of 300° C. and is not affected by body fluids. For example, tubing which may be used for this purpose is commercially available from Micro ML Tubing Sales, 45–10 94th Street, Elmhurst, N.Y. 11373.

The reaction mixture is injected into each of the tubes and each tube is closed at both ends, preferably with a bubble at each end so as to isolate the reaction mixture from the ends of the tube. The clamp or other closure at one end is small enough to fit through the wire mesh screen. The clamp at the other end is preferably too large to fit through the screen. After injecting the reaction mixture into as many of the tubes as desired, a plurality of the capillary tubes are threaded through and suspended by the wire mesh. The bundle of tubes and the mesh are installed in the reaction chamber 106 and the chamber closed and sealed. The clamp 144 is simply a heat sealed end of the capillary tube 140 which forms an enlarged clamp. The computer is then activated to begin switching the fluid flows through the chamber 106 around the capillary tubes as above described.

Figure 10:
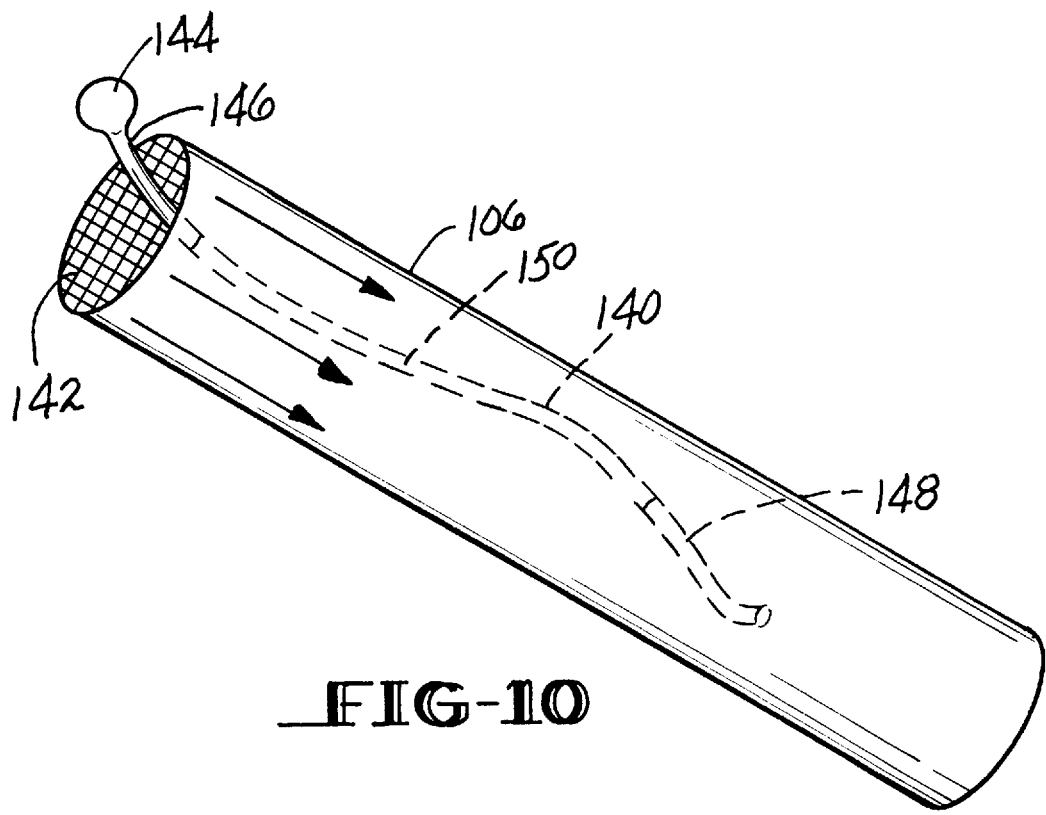
FIG. 10 is a simplified view of the reaction chamber of the apparatus shown in FIG. 5 showing an exemplary single capillary reaction tube held in place by a wire mesh.

FIG. 10 shows an exemplary capillary tube arrangement in the reaction chamber 106. In this Figure, a single capillary tube 140 is shown held in place in the reaction chamber 106 by a wire screen 142 across one end of the reaction chamber 106. The tubing clamp 144 at the upstream end of the capillary tube 140 holds the capillary tube 140 in place with the downstream end free to wiggle in the turbulent flow within the reaction chamber 106 because it is too large to fit through the mesh of the screen 142 as mentioned above. Bubbles 146 and 148 in the ends of the capillary tube 140 isolate the reaction mixture 150 from the ends of the tube. In this preferred embodiment, the upstream clamp 144 also bears a coded tab or stamp which served to identify the sample. The paddle-shaped clamp 144 also flutters in the fluid flow, and thus creates turbulence as the circulating fluid passes it.

Figure 11:
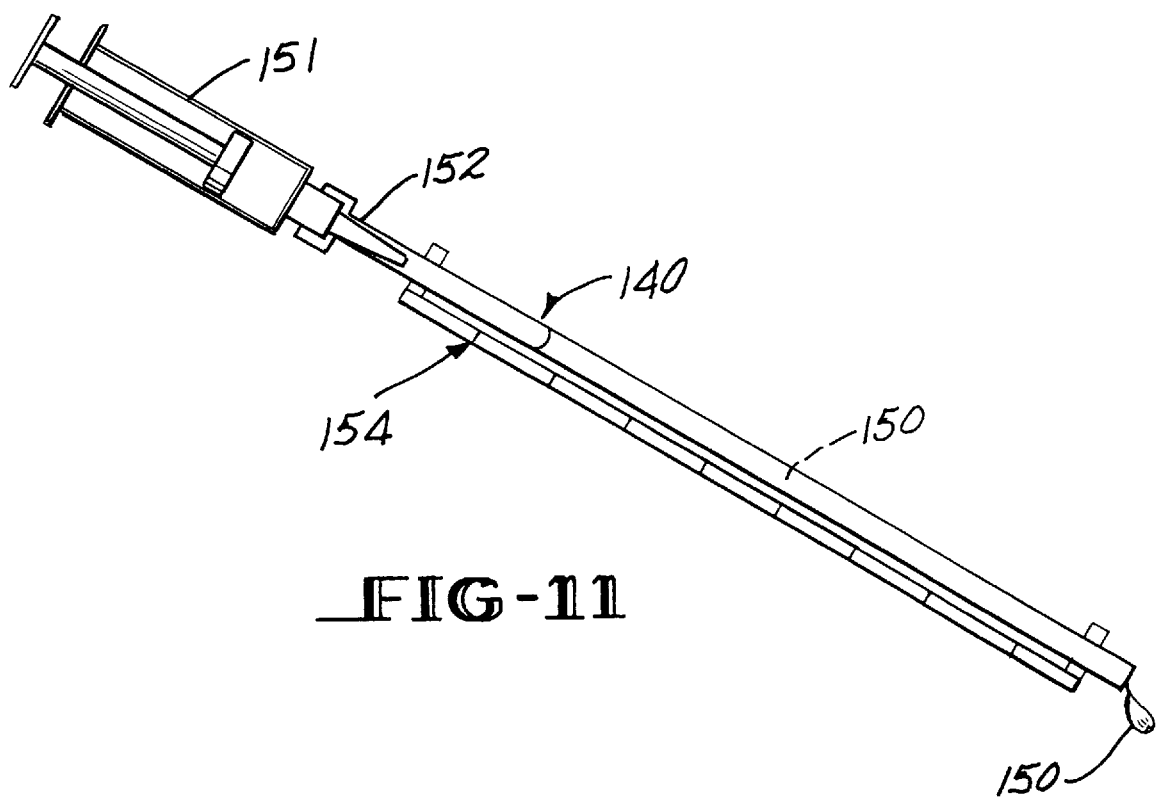
FIG. 11 is a diagram of an apparatus for injection of a reaction mixture into a capillary tube in graduated amounts.

FIG. 11 shows a system for loading the capillary tubes 140 with known amounts of PCR reaction mixture and removing the PCR product after processing. A syringe 151 is inserted into the mouth 152 of the capillary tube 140 with an air-tight fit. The capillary tube 140 may be graduated itself or may be placed in a holder 154 with a graduated scale next to the tube as shown. The open end of the capillary tube 140 is immersed in a reservoir of the reaction mixture 150. The syringe plunger is then withdrawn, sucking enough air out of the capillary tube to lower the pressure therein below atmospheric pressure. The PCR reaction mixture is then pushed into the capillary tube 140 by the higher atmospheric pressure outside acting on the reaction mixture reservoir. The level or amount of reaction mixture is determined by the position of the meniscus within the capillary tube 140. The position of the meniscus will indicate volume uptake within ±2–5%. After filling the capillary tube 140, the ends are sealed, clamped, or capped and PCR processing proceeds. Removal of the finished PCR product is accomplished by cutting the end clamps off the capillary tube 140 and reversing the above process. Note that, in this process, the capillary tube 140 is its own pipette. The syringe never touches the reaction liquid, thereby minimizing the chance of cross contamination.

The fourth embodiment described with reference to FIGS. 5 through 9 has the advantages of being able to process different sample volumes from analytical, to semi-prep scale, and to preparative scale, all at the same time. The volume processed can be changed by altering the capillary tube length, the number of tubes in the reaction chamber, and/or the internal diameter of the tubes. Also, turbulent flow in the reaction chamber accelerates reaction mixture temperature equilibration after a temperature step. Preferably the volume of the reaction chamber is less than 10% of each bath's volume. Variable control by the computer 122 over the flow rate through the chamber can permit optimizing the time response and temperature equilibration time between PCR runs acting on different numbers of capillary tubes and sample volumes where different percentages of the reaction chamber volume are occupied by sample tubes. Very rapid and precisely controlled temperature changes in the temperature of the reaction mixtures in the capillary tubes may be achieved because of the high precision of the fluid bath temperature control, for example, bath precision of ±0.1° C. is available commercially. In addition, the low heat capacity of the capillary tubes, the high rate of heat flow between the reaction mixtures and the heat exchanger fluid, the turbulent flow around the capillary tubes, and the absence of voids in the chamber 106 all aid in minimizing the total PCR protocol time.

An excellent advantage of the instrument shown in FIG. 5, as with many other of the capillary tube PCR instruments disclosed above, is the ability to scale up the volume of finished product produced without the need to engineer a new thermal design for a metal block heat exchanger and without disturbing the thermal cycle parameters. This flexibility can ease the complications of using prior art PCR instruments for PCR-based manufacturing processes. The instrument design shown in FIG. 5 is also inexpensive to build because substantially all of its components, such as the water baths, personal computer, solenoid valves, capillary tubing, syringe, etc., are readily available, off-the-shelf items.

Metal Block Capillary Thermal Cycler

Figure 12:
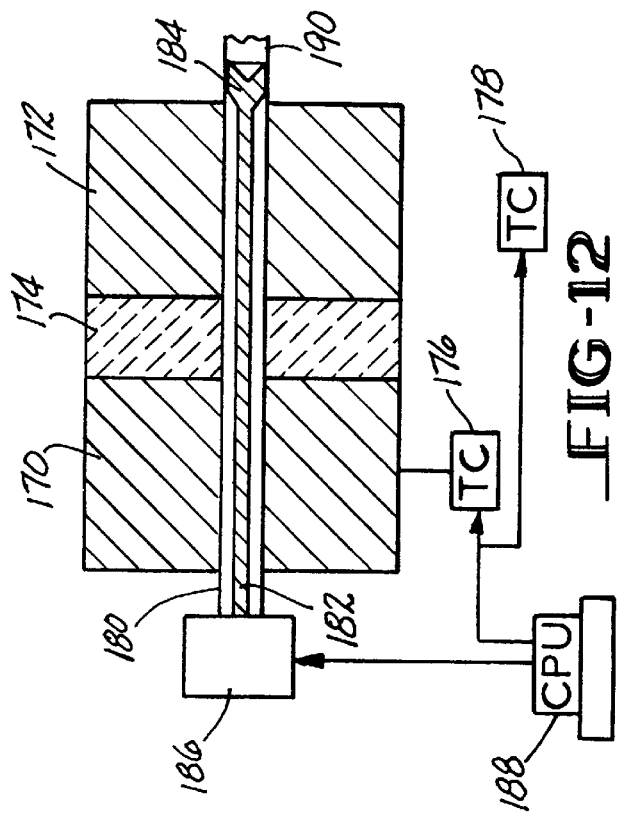
FIG. 12 is a conceptual diagram of a fifth embodiment of a capillary tube PCR instrument using two metal block heat exchangers held at constant temperature and a capillary tube reaction chamber running therebetween in which the reaction mixture is pumped back and forth.

A fifth embodiment of a capillary tube PCR thermal cycler instrument in accordance with the invention is shown in FIG. 12. In its simplest form, this device comprises two metal block heat exchangers 170 and 172 separated by a layer of insulation 174. The heat exchangers 170 and 172 could also be other types of heat exchangers such as thermostatically controlled constant temperature fluid baths. Each metal block heat exchanger 170 and 172 is preferably made of aluminum or some other good heat conducting metal to minimize temperature gradients therein.

The temperature of each metal block is maintained at a constant temperature by any suitable temperature control system such as is symbolized by box 176 for metal block 170 and box 178 for metal block 172. The temperature of metal block heat exchanger 170 is maintained constant in the temperature range suitable for PCR denaturation, typically 92°–98° C. and typically 94° C. by temperature control system 176. The temperature of metal block heat exchanger 172 is maintained constant somewhere in the range of temperatures suitable for PCR annealing and extension (typically 50°–75° C.), such as 60° C. by temperature control system 178. A suitably programmable control system which may be used is disclosed in U.S. Pat. No. 5,038,852 and in U.S. patent application Ser. No. 07/871,264, filed Apr. 20, 1992.

Peltier devices are ideal for controlling the temperatures of the metal blocks because these metal block heat exchangers are each maintained at a constant temperature. Suitable known temperature sensing and feedback control circuits (not shown) are necessary to control the direction of current flow through the Peltier devices to maintain the block temperature constant by extracting heat from the block when it gets too hot and adding heat when it gets too cold. Any other temperature control system will also work for the blocks such as resistance heaters and/or heated/chilled fluid circulating through passages in the metal blocks with the chilled fluid being, for example, tap water or antifreeze chilled by circulating freon of a refrigeration unit, depending upon the desired temperatures of the blocks. The temperature control systems are shown only once in FIG. 12 and are omitted in subsequent drawings illustrating the steps of carrying out the PCR process using the depicted device to avoid unnecessary repetition.

In this embodiment, at least one thin-walled capillary tube reaction chamber 180 runs through the two metal blocks 170 and 172 with a portion of the tube 180 surrounded by the metal block heat exchanger 170 and another portion surrounded by the metal block heat exchanger 172. The thin-walled capillary tube can be plastic, metal, or glass, with plastic being preferred. Glass can interfere with the PCR reaction by causing the template strands or the polymerase to stick to the walls, thereby interfering with the anneal/extend process. Preferably the interconnection between the capillary tube and the metal block heat exchangers is a slight friction fit, if the tube and block are designed to remain stationary relative to each other, such that the capillary tube 180 can be quickly and easily replaced by sliding a new capillary tube into the metal blocks, thereby rendering the capillary tubes disposable. This feature minimizes the risk of cross-contamination and may simplify use of the device by eliminating the need to wash and/or sterilize the capillary tubes between PCR runs. Alternatively, the tubes can be cleaned between PCR runs.

Introduction of a reaction mixture sample and movement within the capillary tube 180 may be accomplished with a positive displacement pumping device such as a syringe or a peristaltic pump. In addition, an air or liquid buffer may be used between the positive displacement pumping device and the reaction mixture sample.

Introduction of a sample and reaction mixture into tube 180 is accomplished as shown in FIG. 12 via an automated syringe. A thin rod 182 forming a piston 184 on one end thereof is inserted into the capillary tube 180 through blocks 170 and 172 by a stepper motor 186. The piston 184 forms a seal with the walls of the capillary tube 180. This stepper motor 186 is controlled by a controller such as a suitably programmed computer 188. The function of the stepper motor 186 could also be performed by a pneumatic system. One end 190 of the capillary tube 180 is in fluid communication with a reservoir (not shown) of sample and reaction mixture during mixture introduction. The stepper motor 186 is actuated to withdraw the piston 184 back through the capillary tube 180, thereby lowering the pressure therein below atmospheric pressure. This process causes the reaction mixture 192 to be pushed or drawn into the capillary tube 180 until there is enough reaction mixture in the tube 180 to completely fill the capillary tube volume within one block as shown in FIGS. 13 and 14.

Figure 13:
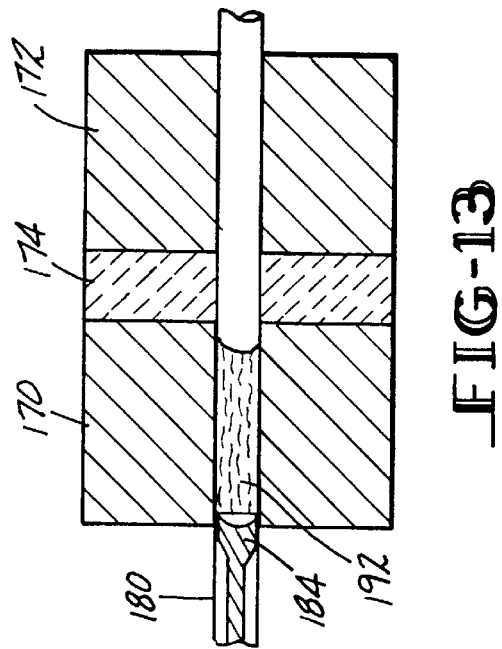
FIG. 13 is a diagram of the PCR instrument shown in FIG. 12 at the denaturation stage of a PCR protocol.

During denaturation, shown in FIG. 13, the controller 188 and stepper motor 186 position the rod 182 and piston 184 at the left edge of the heat exchanger 170 so that the reaction mixture 192 inside the capillary tube 180 is contained within the heat exchanger 170. The reaction mixture 192 is thus rapidly heated to 94° C. The piston 184 remains in this position for a time determined by data stored in the computer 188 defining the desired time for the denaturation incubation of one cycle of the PCR protocol. These data either can be programmed into the controller by the user through a user interface or permanently stored in the memory of the controller.

Figure 14:
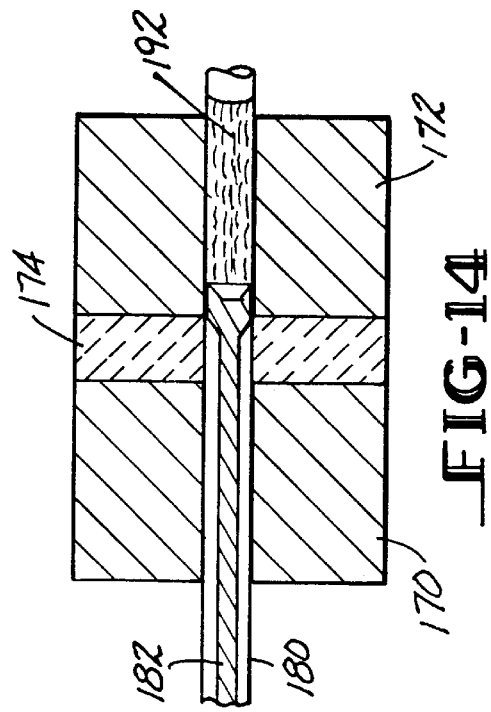
FIG. 14 is a diagram of the PCR instrument shown in FIG. 12 at the anneal/extend stage of a PCR protocol.

The anneal/extend incubation is started when the computer 188 and stepper motor 186 move the rod 182 and piston 184 in the direction to push the reaction mixture 192 to a position in the capillary tube that is completely surrounded by the heat exchanger 172 as shown in FIG. 14. Here, the reaction mixture is rapidly cooled to a temperature of between 50°–70° C. and typically 60° C. to cause the primers to anneal to the single-stranded templates and begin formation of the long extension product. At the completion of the anneal/extend incubation, the mixture 192 is then ready for a new cycle of denaturation as in FIG. 13 to split the double-stranded extension product into single-stranded templates.

The controller and stepper motor then withdraw the rod 184 and piston 182 and mixture 192 back into the heat exchanger 170 to begin another denaturation incubation. The cycle of incubations is repeated the number of times programmed by the user or stored permanently in the database of the computer 188.

Figure 15:
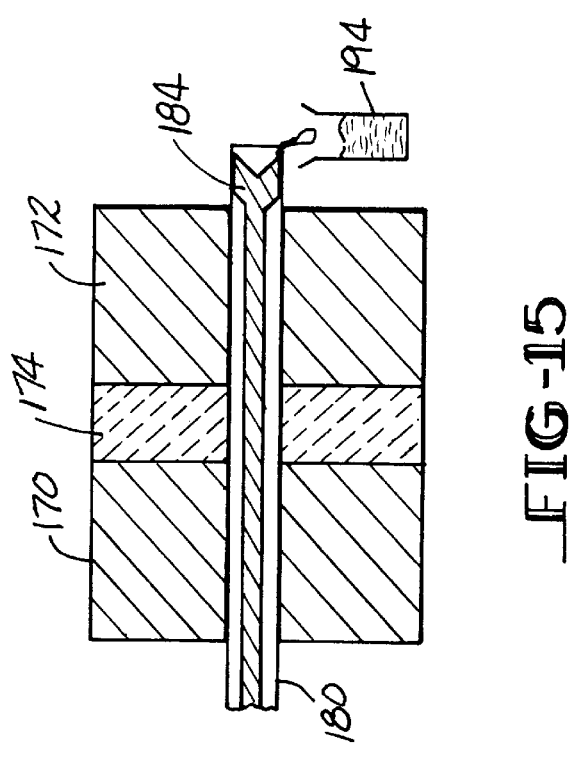
FIG. 15 is a diagram of the PCR instrument shown in FIG. 12 at the finished product ejection stage of a PCR protocol.

After the PCR protocol has been completed, the reaction mixture 192 is discharged into a suitable receptacle as shown in FIG. 15. The piston pushes the mixture 192 through blocks 170 and 172 and out of the capillary tube 180 into a container 194.

Figure 16:
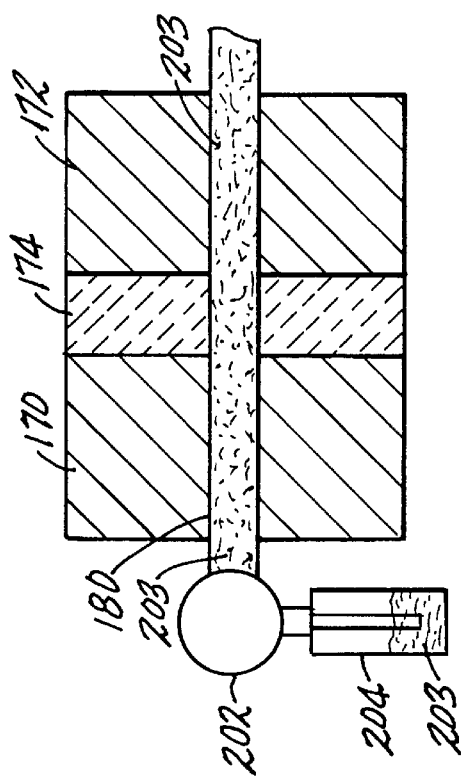
FIG. 16 is a diagram of an alternative fifth embodiment of the PCR instrument shown in FIG. 12 at the sample introduction stage of a PCR protocol.
Figure 17:
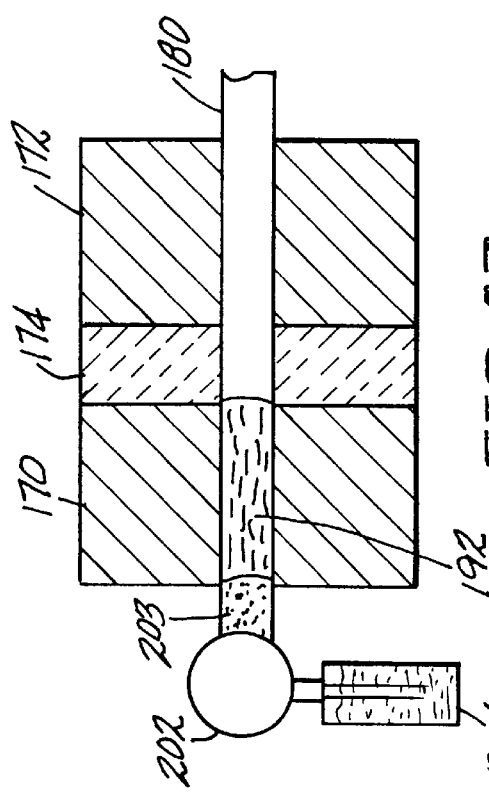
FIG. 17 is a diagram of the PCR instrument shown in FIG. 16 at the denaturation stage of a PCR protocol.

FIGS. 16–19 illustrate an alternative fifth embodiment of a capillary PCR instrument similar to that just described except that the function of the rod 182 and piston 184 are replaced by an inert oil 203. The inert oil 203 is directed through a sample valve loop 202 from an oil reservoir 204. The oil may be either pumped or driven under pneumatic pressure through the sample valve loop 202 so as to push and pull the PCR reaction mixture back and forth in front of it between the block 170 and block 172. This pumping or pneumatic action on the oil is under the control of a computerized controller (not shown) which responds to stored data defining the desired PCR protocol. The valve loop position and reservoir pressure are computer controlled via a stepper motor initially to fill completely the capillary tube 180 with oil as shown in FIG. 16. A reaction mixture sample 192 is then pulled into the tube 180 as the oil 203 is withdrawn back into the reservoir 204 until the reaction mixture sample 192 is entirely surrounded by the heat exchanger 170 as shown in FIG. 17 for the denaturation incubation.

Figure 18:
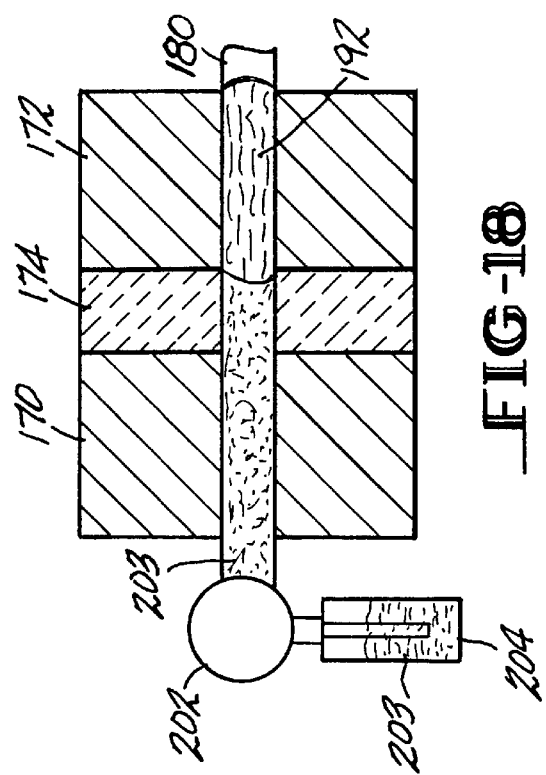
FIG. 18 is a diagram of the PCR instrument shown in FIG. 16 at the anneal/extend stage of a PCR protocol.
Figure 19:
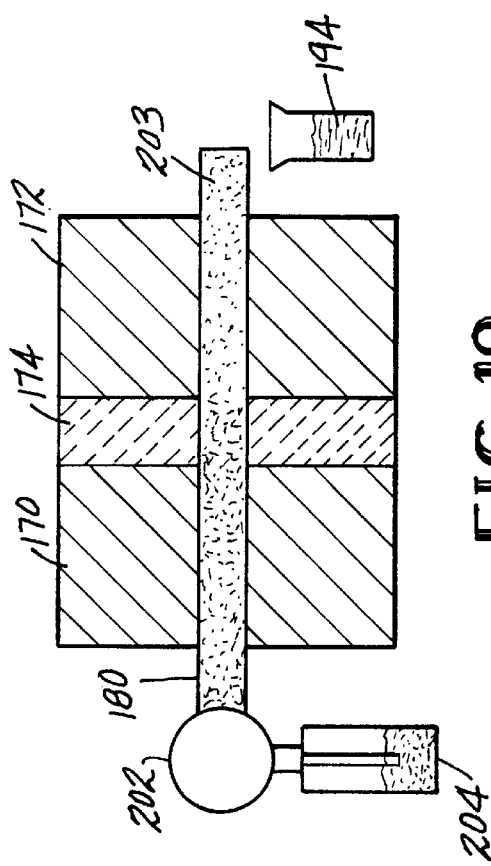
FIG. 19 is a diagram of the PCR instrument shown in FIG. 16 at the sample ejection stage of a PCR protocol.

After the denaturation incubation is complete, the oil 203 is again pumped further by the controller so as to push the PCR reaction mixture to a position in the capillary tube where it is completely surrounded by the heat exchanger 172 as shown in FIG. 18. There, the mixture is rapidly cooled to the anneal/extend temperature. Upon completion of the anneal/extend incubation, the controller (not shown) will reverse the direction of the inert oil so as to draw the PCR reaction mixture back into the heat exchanger 170 to start a new cycle. This cycle of incubations is repeated the number of times specified in the PCR protocol data stored in the programmable controller. After the required number of cycles is completed, the controller issues a control signal to pump the oil far enough through the capillary tube 180 to expel the finished product into a collection container 194 or a sample detection system coupled to the end of the capillary tube 180 which is not coupled to the sample valve loop 202.

The samples also may be drawn into capillary tubes as above described to a stationary position and then either the capillary tubes or the heat exchange blocks are moved relative to one another to perform the thermal cycling on the reaction mixture sample. In one such embodiment, the tubes and samples remain stationary an d the blocks are translated back and forth. In another, the blocks remain stationary and the tube containing the reaction mixture is translated between them. In these embodiments, there must be relatively low friction between the blocks and the thin capillary tube to facilitate movement. This feature decreases the thermal conductance between the block and tube and therefore limits the thermal response and thus increase overall cycle time. Thermal conductance could be maximized in these alternative embodiments by the use of a thermally conductive grease or other lubricant such as mineral oil or ethylene glycol polymer.

Metal Block Multiple Capillary Thermal Cycler

Figure 20:
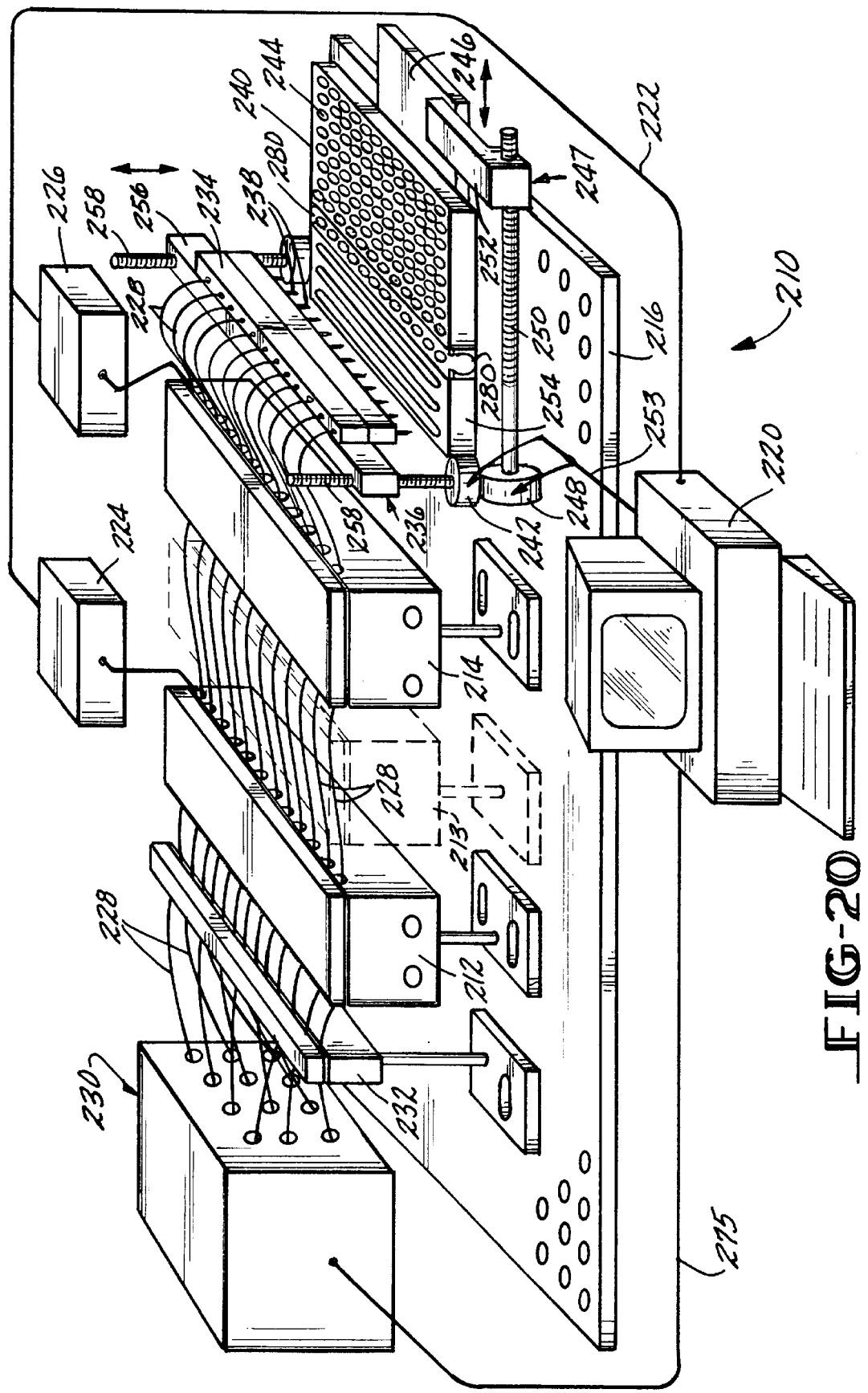
FIG. 20 is a simplified perspective view of a sixth embodiment of a PCR apparatus for an array of capillary reaction tubes in accordance with the invention.

A "breadboard" layout of a sixth embodiment of the present invention is illustrated in FIG. 20. The breadboard capillary thermal cycling apparatus 210 comprises at least 2 metal-block heat exchangers 212 and 214 which are, in this preliminary design, fixed to a bed plate 216. A third heat exchanger 218, shown in dashed lines in FIG. 20, m ay be positioned i n between heat exchangers 212 and 214 if a protocol requiring separate annealing and extension temperatures is utilized. Heat exchangers 212 and 214 are separated by an air gap which insulates the two heat exchangers from one another. Alternatively, they may be separated by any suitable insulative layer such as glass, wool, or a foamed polymer. A personal computer 220 communicates input control data via line 222 to thermostatic controllers 224 and 226. These controllers maintain each heat exchanger 212 and 214 at a constant temperature for either denaturation (typically 94° C. or 95° C.) or annealing and extension (between about 37°–65° C. and typically 60° C.). A plurality of capillary tubes 228 are routed from a sample transfer device 230, through a support clamp 232, through each of the heat exchangers 212 and 214, and through a clamp bar 234 on a tube lift assembly 236.

Each of the capillary tubes is made of DuPont Teflon® and preferably has an internal diameter of about 1.5 mm and a wall thickness of about 0.3 mm. This tubing may be obtained from Zeus Industrial Products, Inc. The tips 238 of the capillary tubes 228 are arranged in a linear row vertically over a microtiter tray 240 by the tube lift assembly 236. A computer-controlled stepper motor 242 rotates lead screws which raise and lower the clamp bar 234 to in turn raise and lower the tube tips 238 into and out of a row of sample containers 244 arranged with tray 240. In this embodiment, twelve capillary tubes 228 are provided to be able to simultaneously handle one entire row of sample containers 244 in wells in the 96-well microtiter tray 240. However, other numbers of simultaneously operating reaction tubes are clearly compatible with the invention.

The breadboard apparatus 210 uses cartridge heaters embedded in heat exchanger blocks 212 and 214. The temperature controllers 224 and 226 for the cartridge heaters are Watlow 922A210 real-time proportional temperature controllers, which have RTD or thermocouple temperature sensors embedded in the thermal cycler blocks 212 and 214 (not shown). Other regulated heat sources could also be used such as surface-mounted electrical heaters or fluids circulated from constant temperature reservoirs.

The microtiter tray 240 is typically a plastic tray having an 8 by 12 array of wells, each well holding a plastic sample container 244. The tray 240 is mounted on a movable platen or sliding stage 246, part of a translation assembly 247. The translation assembly 247 comprises the stage 246, a stepper motor 248 mounted on a base plate 216, and a lead screw 250. The stepper motor 248 is controlled by the computer 220 and is connected through the lead screw 250 to a fixed arm 252 which is attached to the stage 246. The stepper motor 248 rotates the lead screw 250 to index the stage 246 back and forth to various positions under the lift assembly 236. Both the stepper motor 248 and the stepper motor 242 are programmably controlled by computer 220 via line 253.

Mounted adjacent to the microtiter tray 240 on the stage 246 is a cleaning tray 254. An enlarged partial side view of the stage 246 and trays 240 and 254 is shown in FIG. 21. The tray 254 has three parallel troughs, C, R, and W. These troughs contain a cleaner, a rinse liquid, and a waste drain, respectively. The cleaner may be a 10% solution of chlorine bleach. The rinse solution may be 2.8 Molar sodium thiosulfate, as set forth in Prince, A. M. and Andrus, L., "PCR: How to Kill Unwanted DNA", *BioTechniques* 12, #3, 358–360 (1992). This tray 254 is used to clean and rinse the capillary tubes 228 before the stage 246 is indexed between rows of sample containers 244. The cleaning tray 254 may be connected to fluid supply reservoirs to keep the cleaner and rinse troughs full and to a waste container to receive waste discharge from the waste drain. The trays 240 and 254 are removably mounted on the sample stage 246. The sample stage 246 is indexed back and forth under computer control via line 253 to stepper motor 248 so as to align the row of capillary tube tips 238 above the appropriate trough or sample row.

The tube lift assembly 236 comprises a drive bar 256 which rides on bearings which turn on a pair of lead screws 258. The lead screws 258 are synchronously driven by the computer controlled stepper motor 242 to raise and lower the drive bar 256. The clamp bar 234 is bolted to the drive bar 256 and includes a bolted plate which clamps the tips 238 of the capillary tubes 228 in a vertical orientation over the translator assembly 247 which horizontally positions the cleaning tray 254 and the microtiter tray 240.

The sample transfer device 230 in this breadboard design is more clearly shown with its cover removed in FIG. 22. Sample transfer device 230 includes a fixed stage 260 which has up to twelve syringes 262 connected to the capillary tubes 228 and horizontally mounted and clamped in a spaced array in the fixed stage 260. The cylinders 264 of the syringes 262 may be connected to the ends of the capillary tubes 228 individually or they may be ganged together. For example, a total of six syringes 262 may be used with each syringe feeding two capillary tubes 228.

The plungers 266 are captured between a movable plunger clamping plate 268 and clamping bar 270. The clamping plate 268 is mounted on a horizontally slidable stage 272 driven by a stepper motor 274. The stepper motor 274 is controlled by computer 220 via line 275 and moves stage 272 back and forth in order to aspirate, translate, and discharge the PCR reaction mixture sample in each of the capillary tubes 228. Optionally, the syringes may be replaced with one or more peristaltic pumps to perform the same function.

This sixth embodiment operates under computer control through a tube-cleaning cycle prior to each PCR protocol performed on a row of samples. First, the sample stage stepper motor 248 indexes the sample stage 246 to a position at which capillary tube tips 238 are directly over the cleaner trough C. The lift assembly 236 stepper motor 242 then lowers the tube tips 238 into trough C. The stepper motor 274 in the sample transfer device 230 is then energized to withdraw the plungers 266 to aspirate a slug of cleaner fluid such as bleach into the capillary tubes 228 to a position past the thermal platens 212 and 214. The lift assembly 236 then raises the tips 238 from the fluid in the trough C. The sample stage 246 is then moved horizontally via stepper motor 248 to position the waste trough W under the capillary tube tips 238. The sample transfer device 230 is then oscillated back and forth to move the cleaner back and forth in the capillary tubes 228 a predetermined number of times and distances to ensure complete cleansing. When this clean cycle is ended, the lift assembly 236 then lowers tips 238, via stepper motor 242, into the trough "W". At this point, the sample transfer device 230 inserts the plungers 266 to expel the cleaner from the capillary tubes 228 into the waste trough W.

Second, the lift assembly 236 then raises the tube tips 238 out of the waste trough "W", and the sample stage 246 is then indexed to position the tube tips 238 over the rinse trough "R". The lift assembly 236 then lowers the tips 238 into the rinse trough "R", and the sample transfer device 230 then aspirates rinsing solution into the capillary tubes 228. The rinsing solution may include a reducing agent such as sodium thiosulfate to restore tube condition in preparation for the next PCR run. The tube tips 228 are then raised and the sample transfer device 230 again may be oscillated back and forth as required to effectively rinse the capillary tubes. The lift assembly 236, transfer device 230, and translator assembly 247 are then operated to position the row of capillary tube tips 238 over the waste trough "W" and discharge the rinse fluid from the capillary tubes 228 into the waste trough.

Third, the lift assembly 236 and translator assembly 247 are then operated under command of computer 220 to position a row of sample containers 244 under the capillary tube tips 238. The lift assembly 236 then lowers the tube tips 238 into the sample containers 244, and the stepper motor 274 of the sample transfer device 230 withdraws plungers 266 aspirating a predetermined quantity of reaction mixture sample into an initial position within each of the capillary tubes 228. The stepper motor 242 of the lift assembly 236 is then actuated in reverse to lift the tips 238 out of the row of the sample containers 244.

The stepper motor 274 then continues to withdraw the plungers 266 to pull these reaction mixture samples in the capillary tubes 228 through the tubes through the thermal heat exchanger 214 to a position in which the samples are fully within the heat exchanger 212. The stepper motor 274 is operated intermittently to slowly move the samples between the tube tips 238 and the heat exchanger 214. The intermittent movement permits the fluid at the rear meniscus of the sample slug to catch up to the main body of the sample slug without forming a separate bubble in the capillary tube. This effect of surface tension may be minimized by maintaining the length of capillary tube outside the heat exchangers 212 and 214 at elevated temperature. However, since the breadboard apparatus 210 described here was operated in a room temperature environment, intermittent movement of motor 274 was required in order to allow the fluid in the meniscus to catch up to the main body of the sample slug. This phenomenon is often called "dragout". Dragout may also be minimized by minimizing the internal surface roughness of the tubing and/or coating the interior walls with a polymer such as parylene.

Once the samples reach heat exchanger 214, stepper motor 274 may be operated continuously to position the samples fully within heat exchanger 212. The first incubation of the PCR protocol begins when the samples are fully positioned in the heat exchanger 212. The plungers 266 are then alternately inserted and withdrawn via stepper motor 274 to translate the reaction mixture samples between the heat exchangers 212 and 214 in accordance with the PCR protocol stored in the computer 220. At the completion of the protocol, the stepper motor 242 of the lift assembly 230 again lowers the capillary tube tips 238 into the sample containers 244. The stepper motor 274 then energizes to insert the plungers 266 to discharge the PCR product back into the sample containers 244.

The cleaning cycle and thermal cycling steps are then repeated as just described for the next row of sample containers 244 in the microtiter tray 240. Operation of the stepper motors in the above described process is programmed into the computer 220 by the user. The steps programmed may be varied and may include discharge of the PCR product to a different row of sample containers 244 than as described above. The above sequence is illustrative only.

Optionally mounted between the microtiter tray 240 and the cleansing tray 254 is a capillary tube pressure seal fixture 280. Fixture 280 is shown in FIG. 21 and an enlarged sectional view is shown in FIG. 28. This seal fixture 280 is a plastic or metal block 282 with one row of 12 wells 284 which may be aligned beneath the row of capillary tube tips 238. Each well 284 may be encircled by an O-ring seal 286 mounted in a recess in the top surface of the block 282 or one continuous O-ring 286 may extend around all 12 wells 284. The block 282 is designed to mate with the bottom surface of the clamp bar 234 as shown in FIG. 28 with the O-ring seal 286 compressed therebetween and the tube tips 238 enclosed within the wells 284. The capillary tubes 228 are either press fitted through a one piece clamp bar 234 or the clamp bar 234 may be a two piece arrangement with an O-ring seal 288 sandwiched between the upper and lower pieces around each capillary tube 228 as is shown in FIG. 28.

The pressure seal fixture 280 permits the samples in the capillary tubes to be translated in a pressurized environment during the PCR protocol. The fixture is preferably used in situations when the apparatus is operated at high elevations where the boiling point of the reaction mixture sample is equal to or less than the denaturation temperature called for in the PCR protocol. However, use of this fixture may be avoided by the addition of a denaturant such as formamide to the reaction mixture. The addition of a denaturant lowers the temperature required for denaturation and also slightly raises the boiling point of the solution.

If the samples need to be cycled in a pressurized environment during performance of the protocol, the sample handling sequence previously described is slightly modified. Instead of withdrawing a reagent mix sample into the heat exchanger 212 to start the protocol, the sample transfer device 230 continues to aspirate the sample to a position that is a predetermined distance beyond the heat exchanger 212. The lift assembly 236 and translator assembly 247 then move to position the tube tips 238 over the fixture 280 and then lower the tips 238 into the wells 282 until the O-ring seal 286 is compressed between the fixture 280 and the underside of the clamping bar 234. In this position, tubes 228 are now isolated from ambient environmental pressure. The sample transfer device 230 then pushes the samples in the capillary tubes 228 back into the heat exchanger 212 for the first denaturation incubation, simultaneously pressurizing the sample volume, the air within the capillary tubes, and the enclosed air volume beneath the tube tips 238 in the sample wells 284 to a minimum pressure above atmospheric. Sample transfer device 230 is then operated to position the samples alternately between the heat exchangers 212 and 214 to execute the thermal cycling protocol in accordance with the instruction data set provided by the user into the computer 220.

Rotary Thermal Platen Capillary PCR Thermal Cycler

A seventh embodiment 298 of the capillary thermal cycler apparatus in accordance with the present invention is shown in FIGS. 23 through 27. This embodiment is similar to the sixth embodiment 210 just described except that the heat exchanger blocks 212 and 214 have been replaced by a rotary cylindrical drum heat exchanger assembly 300. Operation of the seventh embodiment 298 is identical to the sixth embodiment just described in the sample handling aspects. The principal difference lies in the operation of the heat exchanger assembly 300. The heat exchangers assembly 300 is moved relative to the capillary tubes 228 in this embodiment while the samples in the capillary tubes 228 remain stationery.

Figure 24:
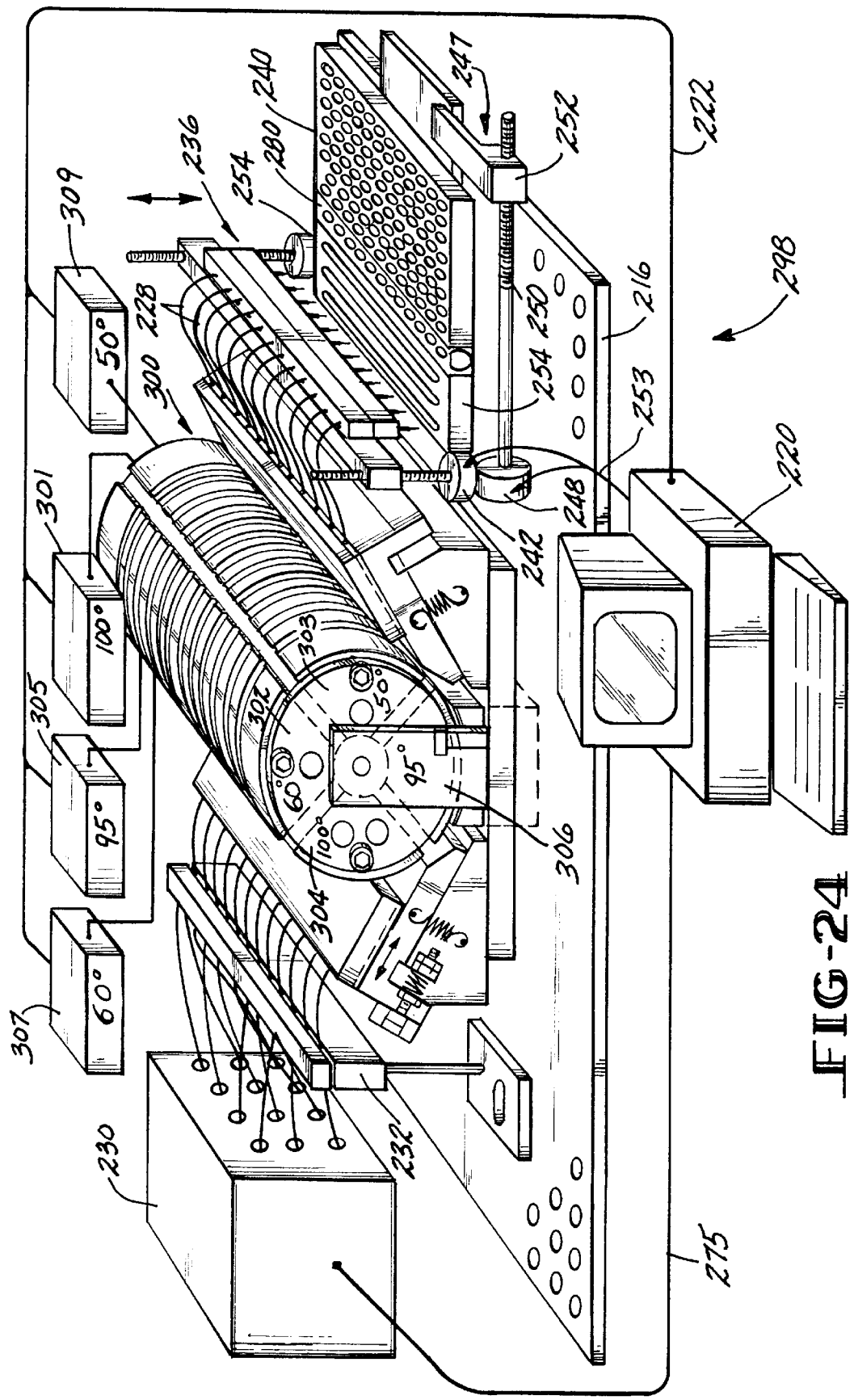
FIG. 24 is a perspective view of a breadboard version of the capillary PCR apparatus shown in FIG. 23.

Like numbers from the sixth embodiment will be used to describe like components in the seventh embodiment in the following description. A simplified side view of this seventh embodiment is shown in FIG. 23. A perspective view of the apparatus 298 is shown in FIG. 24.

In this apparatus 298 a microtiter tray 240, a pressurization fixture 280, and a cleaning trough plate 254 are translated by a translator assembly 247 back and forth beneath a capillary tube tip-lift assembly 236 under computer control via bus line 253 from personal computer 220 as previously described. A sample-transfer device 230 is actuated to draw a reaction mixture sample into the capillary tube tips 238 and then into a position immediately under the heat exchanger 300. However, in this embodiment, the sample is not translated back and forth during the PCR protocol. The sample remains stationary and the heat exchanger assembly 300 is rotated to subject the samples to the various temperature incubations of the protocol. As in the sixth embodiment, the thermal cycling apparatus 298 of the seventh embodiment utilizes sample transfer device 230, a ganged syringe assembly, as shown in FIG. 22. The sample transfer device 230 may also be a peristaltic pumping arrangement, or a pneumatic pumping device, all automatically controlled by computer 220 via bus line 275. The translation assembly 247 indexes the microtiter tray 240, cleaning tray 254, and pressurization fixture 280 under the row of capillary tube tips 238. The lift assembly 236 raises and lowers the capillary tube tips 238 into and out of the sample containers 240, troughs C, R, and W, and the sample wells 286 as previously described.

The heat exchanger 300 is a cylindrical drum-shaped body divided into four, axially extending, wedge-shaped segments 302, 303, 304, and 306, each separated from the other by the legs of an "X" shaped radial insulating layer 308. The drum segments 302 and 306 are utilized for the PCR incubations. Segment 302 is typically maintained at about 60° C. or another temperature corresponding to the annealing and extension temperature by temperature controller 301. Segment 306 is maintained at the denaturation temperature, typically 95° C., by temperature controller 305. The other two segments 303 and 304 are transitional segments. The temperature of these segments will range between 2° C. and 20° C. higher or lower than the incubation segments 302 and 306. Segment 304 is maintained at a temperature between 2° C. and 20° C. above the denaturation temperature of approximately 95° C. at which the segment 306 is maintained and is typically at about 100° C. maintained by temperature controller 307. The segment 304 is used to accelerate the transition, i.e. increase the ramp rate from the annealing/extension temperature to the denaturation temperature, to minimize the total protocol period. In contrast, the remaining segment 303 is maintained at a temperature significantly below the annealing and extension temperature of typically about 60° C. Segment 303 is maintained in a range of between about 2° to 20° C. below the extension temperature and is typically maintained at about 50° C. by the temperature controller 309.

The seventh embodiment 298 with four heat exchange segments, 302, 303, 304, and 306, is believed to be optimal for a PCR protocol in which a single denaturation incubation temperature and a single annealing/extension incubation temperature are used. The third and fourth segments, 303 and 304, kept at a higher and a lower temperature, respectively, than the incubation temperatures, are preferred in order to maximize efficiently the ramps up and down between the annealing/extension temperatures and the denaturation temperature, as these transition times should be minimized in order to maximize the production of the reaction product in a given time period. It should be understood that alternative embodiments are envisioned which have a different number of segments, such as two, three, or more segments, depending on the particular protocol required to be performed. For example, a five or six segmented heat exchanger could be optimized for either two- or three-temperature incubation protocols.

The heat-exchange assembly 300 is preferably rotated back and forth to maintain the temperatures within the required limits in order to minimize the complexity of fluid and/or electrical connections to the segments. In the breadboard embodiment 298 illustrated, the segments are maintained at temperature by heaters embedded in each aluminum segment. In addition, an RTD or thermocouple is embedded in each segment to provide the necessary control signals to the temperature controllers 301, 305, 307, and 309. The heat-exchange assembly 300 could, alternatively, be rotated in one direction continuously if suitable slip-ring electrical connections are made to supply heater current and provide temperature detection and control. This alternative may be preferable in a production machine to minimize lead wire fatigue.

Figure 25:
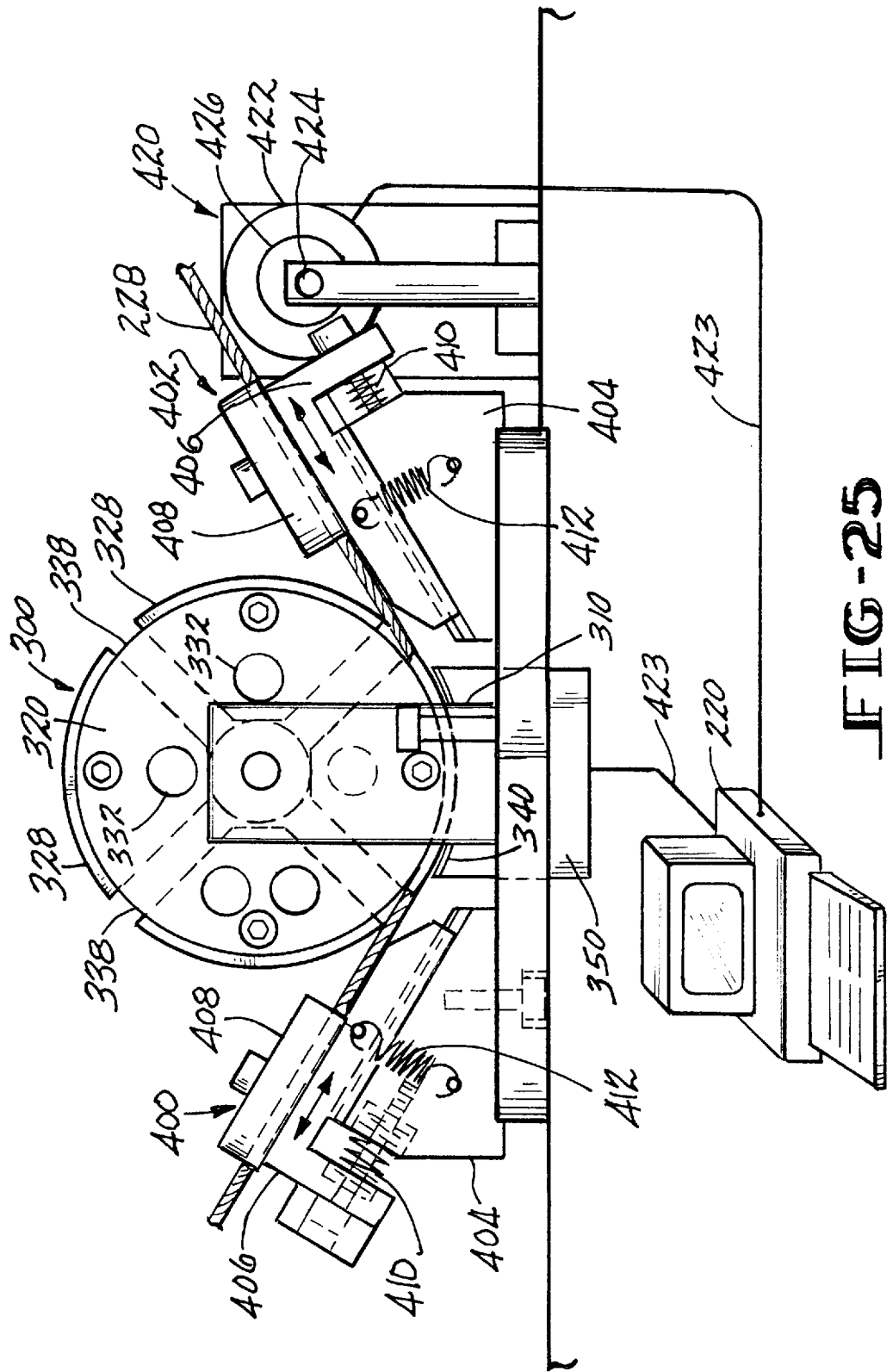
FIG. 25 is an enlarged partial front view of the rotating drum thermal heat exchanger assembly in the apparatus shown in FIG. 24.
Figure 26:
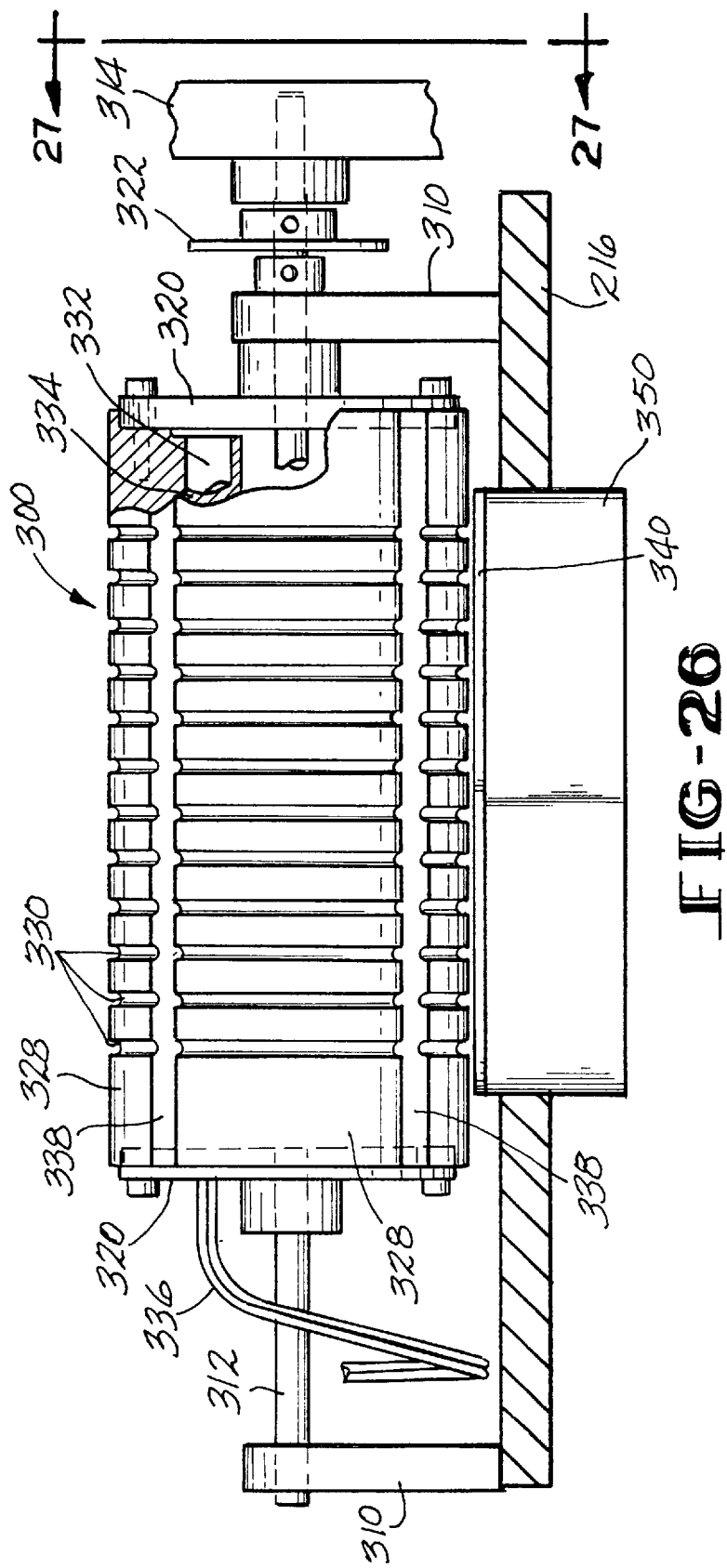
FIG. 26 is a partial side view of the rotating thermal heat exchanger assembly shown in FIG. 24.

A side view of the rotating heat exchanger assembly 300 is shown in FIG. 26. A rear view of the heat exchanger assembly 300 is shown in FIG. 27. The heat exchanger assembly 300 is horizontally and rotatably supported from the breadboard base plate 216 by two stationary support posts 310. Each support post houses a bearing (not shown) which in turn rotatably supports an axial shaft 312. The axial shaft 312 has a pulley 314 fixed to one end which is in turn connected via a belt 316 to a stepper motor 318 as shown in the end view of FIG. 25. The stepper motor 318 is connected to and controlled by computer 220. Each of the segments 302, 303, 304, and 306 are wedge shaped, solid aluminum segments, with opposite ends bolted to circular end plates 320. The end plates 320 are, in turn, each fixed to the axial shaft 312 which rides in the bearings held by the stationary support posts 310.

An indexing disk 322 is also fixed to the shaft 312 adjacent to the pulley 314. This disk is coupled to an optical position sensor 324 mounted on the stationary post 310 at the pulley end of the shaft 312. The position sensor 324 is connected through the computer 220 to the stepper drive motor 318. This optical position sensor detects the presence of a notch 326 in the disk 322 to indicate to the computer 220 when the heat exchange drum 300 is correctly positioned.

Each of the segments 302, 303, 304, and 306 preferably has a curved outer surface 328 with twelve, parallel, semicircular grooves 330 therein equally spaced along the length of the segment. Each groove 330 is sized to receive one of the capillary tubes 228 so that at least half of the circumference of the tube 228 is in full contact with the outer surface 328 of the segment. The space between each of the segments is preferably filled with a thermally insulative material such as fiberglass, plastic, or air. The objective here is to minimize the heat transfer among segments 302, 303, 304, and 306.

Each segment 302, 303, 304, and 306 has an axially extending bore 332 therethrough receiving a heater element 334. A single resistance-heater element 334 is utilized in each segment in the embodiment 298 illustrated. However, dual elements also could be used. Each segment also contains a recess for an RTD or thermocouple temperature detector for temperature control. In addition or alternatively, each segment could have one or more flow channels therethrough, through which a constant temperature fluid is circulated to maintain the segment temperature within the required limits. Each heater element and temperature detector is connected to its controller 301, 305, 307, or 309 via a conventional lead wire 336.

Since the heat-exchanger drum 300 is rotated and the sample is maintained in a static position during thermal cycling, tensioning devices 400 and 402 are provided to reduce the wear on the capillary tubes 228 during operation and ensure consistent thermal contact between the tubes and the heat exchanger. Referring now to FIG. 25, each of the tensioning devices 400 and 402 includes an inclined stationary support block 404 mounted on bed plate 216 and a sliding block 406 and cap 408 bolted to the block 406 which clamps the capillary tubes 228 in parallel positions. The blocks 406 and caps 408 position the capillary tubes 228 along a tangent line to the grooves 330 in the surface 328 of the segments of the heat exchanger assembly 300. Each of the sliding blocks 406 is spring-biased away from the heat exchanger 300 in the tangential direction by coil springs 410. A pair of retaining springs 412 acting normal to the surface of the blocks 406 are used to retain the each of the sliding blocks 406 against the inclined upper surface of each of the stationary support blocks 404.

The tensioning devices 400 and 402 are positioned on the bed plate 216 so that each of the capillary tubes 228 contacts the entire groove length of the curved outer surface 328 of each particular segment 302, 303, 304, and 306 when the respective segment is positioned at a "six o'clock" position as is shown in FIGS. 24 and 25. The springs 410 and 412 cooperate to ensure that the portions of the capillary tubes 228 under the heat exchanger 300 are maintained in good thermal contact with the outer surface 328 of each segment and that each tube is retained in its groove 330.

In order to reduce wear on the tensioned capillary tubes 228, a tension release mechanism 420, driven by a stepper motor 422, automatically releases the tension on the tubes 228 during rotation between the heat-exchanger segments. A horizontally mounted rotating shaft 424, driven by motor 422 via computer 220 through bus 423, positions an eccentric lobe 426 against the sliding block 406, in opposition to the spring bias of spring 410. The eccentric lobe 426 pushes the sliding block 406 toward the heat exchanger 300 to release tension on the capillary tubes 228 slightly before or simultaneously with a drive signal transmitted from the computer 220 to the heat exchanger stepper motor 318.

Figure 30:
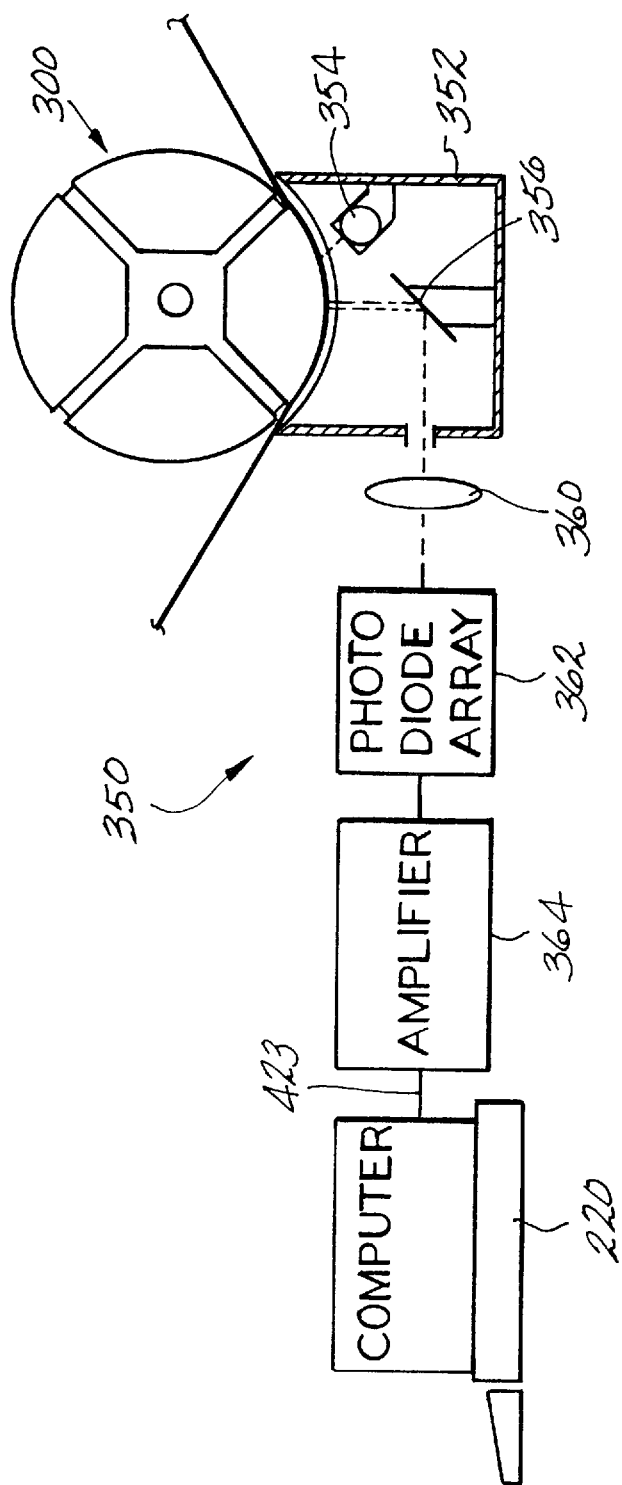
FIG. 30 is a schematic view of a detection system coupled to the seventh embodiment of the invention.

An optically transparent thermal shield 340 may be positioned beneath and closely adjacent to the segment in contact with the capillary tubes 228. This thermal shield 340 may also act as a window to a fluorescence detector 350 mounted under the heat exchanger 300 as shown in FIGS. 26 and 30 to monitor the production of reaction product during the DNA amplification process.

Ethidium bromide, an intercalating dye, is dissolved in the reaction mixture at a level which does not interfere with the PCR. Ethidium ions fluoresce at about 615 nm with a higher intensity when intercalated in the DNA than when free in solution. Consequently, the intensity of fluorescence may be used as a measure of the concentration of the amplified DNA population.

The detector 350 uses a photodiode array (PDA) which detects fluorescence from all twelve of the capillary tubes 228 simultaneously during incubations. The detector 350 is schematically shown in FIG. 30. Mounted beneath the drum 300 and between tensioning devices 400 and 402 is a housing 352 which contains and supports an ultraviolet light source 354 and a mirror 356. The UV source 354 is directed toward the portions of the twelve capillary tubes in contact with the drum 300. The mirror is positioned so that light emitted by or reflected from the capillary tubes under the drum 300 will be directed through an aperture 358 in the housing 352 and through a focusing lens 360 onto a photodiode array 362. The output of the photodiode array 362 is fed through conventional amplifier circuitry 364 to the computer 220 for display.

In this breadboard design, light from each of the 12 capillary tubes is directed to a separate photodiode in the array so that amplification in each tube can be simultaneously and individually monitored. The present diode array used consists of 35 diodes in a linear array. Every third diode is optically coupled as a signal diode to one of the capillary tubes 228. An adjacent diode to each signal diode is used to monitor and electronically subtract background away from the gross signal out of each signal diode.

The annealing/extension section of the drum 300 is positioned against the capillary tubes 228 during monitoring. The detected fluorescence intensity provides real-time monitoring of the growth of PCR product during the PCR protocol. This information also can be used to estimate the amount of target DNA originally present prior to amplification, as, during most of the amplification, the growth rate is a simple exponential process.

The interior of the housing 352 is painted flat black to absorb scattered light and is closely fitted adjacent the bottom of the drum 300 to exclude ambient light. The outer surface 328 of the annealing/extension segment 302 is also painted flat black to absorb scattered light. The curved surface of each of the grooves 330 in the annealing/extension segment 302 is polished to a mirror finish so as to reflect the maximum amount of the fluorescence.

Alternatively, other segments could also be used for detection. However, it is felt that the long duration of the annealing/extension incubation provides the optimal opportunity for monitoring the PCR product buildup from cycle to cycle. In the detector system 350, fluorescence data are received once each second during the annealing/extension incubation. In addition, the entire detection system would preferably be self contained in a production instrument.

The detection system just described may be adapted to many of the embodiments herein described so long as the capillary tubes are relatively transparent so as to pass UV and visible light. In addition, the detection system signal may be used as an input to the computer to calculate and adjust optimum incubation times. Alternatively, the detector output may be used to provide a termination signal for the PCR protocol. In other words, a desired quantity of PCR product could be specified to the computer 220 rather than a total number of cycles as is currently the practice in the art. Finally, other detection systems may be utilized. For example, CCD devices may be used instead of a diode array for enhanced resolution and sensitivity. The detector also may be coupled to a polychromator, and several fluorophores with different emission spectra can be used to distinguish among various components of the reaction mixture. For example, one fluorescent signal, generated by a dye which does not interact with the DNA amplification, can be used to recalibrate the fluorescence optics continuously, compensating for air-bubble formation or solute concentration consequential to solvent evaporation. The optical calibration dye should resist photo-bleaching or, if the DNA-reporting dye photo-bleaches, be chosen to show similar photosensitivity. A second fluorescent signal can be provided by a dye which experiences a strong fluorescence enhancement upon binding to duplex DNA, such as ethidium, the intercalating dye well known in the art of nucleic acid analysis, or a member of the bis-benzimide class of dyes, known to bind to the minor groove of duplex DNA. Higuchi et al, "Simultaneous Amplification and Detection of Specific DNA Sequences," *Biotechnology* 10, Apr. 1992, pp. 413–417, showed that ethidium could be used in the PCR mixture to monitor the accumulation of duplex DNA in real time. Alternatively to this second fluorescent signal, one may attach a dye and a fluorescence quencher to a probe which anneals to PCR template, in such a way that when PCR is performed with a DNA polymerase possessing 5'→3' exonuclease activity, the nick translating activity of the polymerase digests the probe. As disclosed by Holland et al, [PCT Publ. No. WO 92/02638], this digestion activity would generate a fluorescent signal as the dye is split away from the quencher. Use of several, spectrally distinct, fluorophore-quencher pairs attached to probes specific for different templates would allow simultaneous monitoring of accumulation of several PCR products.

The apparatus 298 operates automatically as follows, under control of computer 220. A reaction-mixture sample is drawn into each of the capillary tubes 228 via the lift assembly 236 and sample-transfer device 230 as previously described. The sample is aspirated from the sample containers 244 into the capillary tubes 228 to a position directly under the heat exchanger drum 300. As shown in FIG. 24, segment 306 contacts the section of capillary tube 228 containing the samples. The temperature of the samples in the capillary tubes 228 is quickly raised up to denaturation temperature of 95° C. The denaturation temperature is maintained in the capillary tubes 228 for the required incubation period.

At the end of this period, the assembly 300 is rotated 90° clockwise to position the segment 303 in contact with the capillary tube section containing the reaction-mixture samples. Because the segment 303 is maintained at about 50° C., the samples rapidly cool to a temperature of about 60° C. At an appropriate time, the assembly 300 is rotated another 90° clockwise to position segment 302 against the capillary tube portions containing the samples. The segment 302 is maintained at 60° C. The assembly remains in this position again for the required incubation time dictated by the PCR protocol. At the end of the annealing and extension incubation, the drum is rotated clockwise another 90° so that segment 304 (which has a temperature typically 100° C.) is in contact with capillary tubes 228 for the time necessary to ramp the reaction mix temperature quickly to about 95° C. Upon reaching 95° C., the heat exchanger assembly 300 is rotated quickly counterclockwise another 270° to place segment 306 again in contact with the capillary tubes 228 for the next required denaturation incubation. This process is repeated as required to complete the PCR protocol. During each period of rotation, the cam eccentric 426 is rotated by motor 422 to detension the capillary tubes 228 from the outer surface 328 of the segments. When rotation ceases, the eccentric 426 is rotated to reengage the tensioning devices 400 and 402 to ensure adequate thermal contact during the incubations.

As in the sixth embodiment described above, rotation coordination and control of the heat exchanger assembly and temperature control of the segments is maintained by the computer 220. At the end of the PCR protocol, the computer 220 directs the sample-transfer device 220 to insert the plungers 266 to discharge the reaction product back into the sample containers 244 in the wells in the microtiter tray 240. The cleaning and rinse sequence of steps, described with reference to the sixth embodiment, is then performed to flush the capillary tubes of any contaminants and remnants of the sample just processed. The translator assembly 247 then repositions the microtiter tray 240 to the next row of wells holding sample containers 244, and the entire process is repeated.

The capillary tube tips 238 in the sixth and seventh embodiments above described have a special physical configuration as shown in the enlarged view of a tip 238 in FIG. 29. If the capillary tubes are simply cut off transverse to the axis of the tube, the last drop of sample being discharged often hangs off the end of the tube after dispensing. Thus, complete discharge of the reaction product into the sample well is prevented. It has been found that by tapering the tip wall 290 as shown in FIG. 29, the last drop of reaction product is reliably discharged from the ends 238 of the capillary tube 228.

"Dragout" of the sample in the capillary tubes 228, as the sample is moved back and forth between heat exchangers in the sixth embodiment, and into position under the heat exchanger drum 300 in the seventh embodiment, is minimized in teflon tubing having minimal internal surface rough a surface tension phenomenon in capillary tubing where the fluid adjacent the wall tends to adhere progressively to the wall, creating a generally parabolic longitudinal cross sectional shape to the ends of the sample slug. If the dragout is severe, the trailing end can separate or "drag out" from the main body of the sample slug during slug movement, coalesce, and eventually trap an air bubble between end portions of the sample, thus extending the overall length of the sample. As previously mentioned, the ambient temperature conditions of the samples in the capillary tubes contribute to dragout. Accordingly, maintaining an elevated temperature of the sample and the capillary tube during aspiration into the capillary tubes may minimize dragout. Another effective way to minimize dragout is to break the process of aspirating the sample into position into many discrete steps and pauses. These pauses permit the trailing end of the sample to catch up to the main sample body in the capillary tube.

There is an alternative to using a pressurization fixture 280 at elevations such as Denver, Colo., where the boiling point of water is reduced to 93.5° C. This alternative is the addition of a denaturant such as formamide in the reaction mixture. This approach is suggested in Panaddio et al, "FoLT PCR: A Simple PCR Protocol for Amplifying DNA Directly from Whole Blood," *BioTechniques* Vol. 14, No. 2 (1993) pp. 238–243. The authors used thermostable Tth polymerase rather than Taq polymerase and showed that a 95°–50°–70° C. protocol could be converted to an 85°–40°–60° C. protocol for a reaction mixture containing 18% formamide.

Taq polymerase tolerates a number of DNA denaturants including glycerol and acetamide. In fact, 2.5% formamide in the reaction mixture samples utilized in the seventh embodiment of the invention described above has yielded satisfactory amplification at a denaturation temperature of 89° and a annealing/extension temperature of 63°, thus lowering the protocol temperatures uniformly by about 5° C.

The following paragraphs refer to FIGS. 31–34 which provide a flow chart of the software utilized to control the operation of the seventh embodiment of the present invention. The software in computer 220 controls the five stepper motors. These stepper motors are: motor 274, which operates the syringes 262 in pump 230; stepper motor 318, which drives the heat exchange drum 300; stepper motor 248, which translates the sample stage 246 horizontally; the stepper motor 242, which vertically raises and lowers the tips 238 of the capillary tubes 228; and stepper motor 422, which rotates cam 426 to tension and detension capillary tubes 228 against the heat exchange drum 300.

The software may be programmed in Basic or any other conventional programming language known to those skilled in the art. The present breadboard design described below is programmed in Basic.

Figure 31:
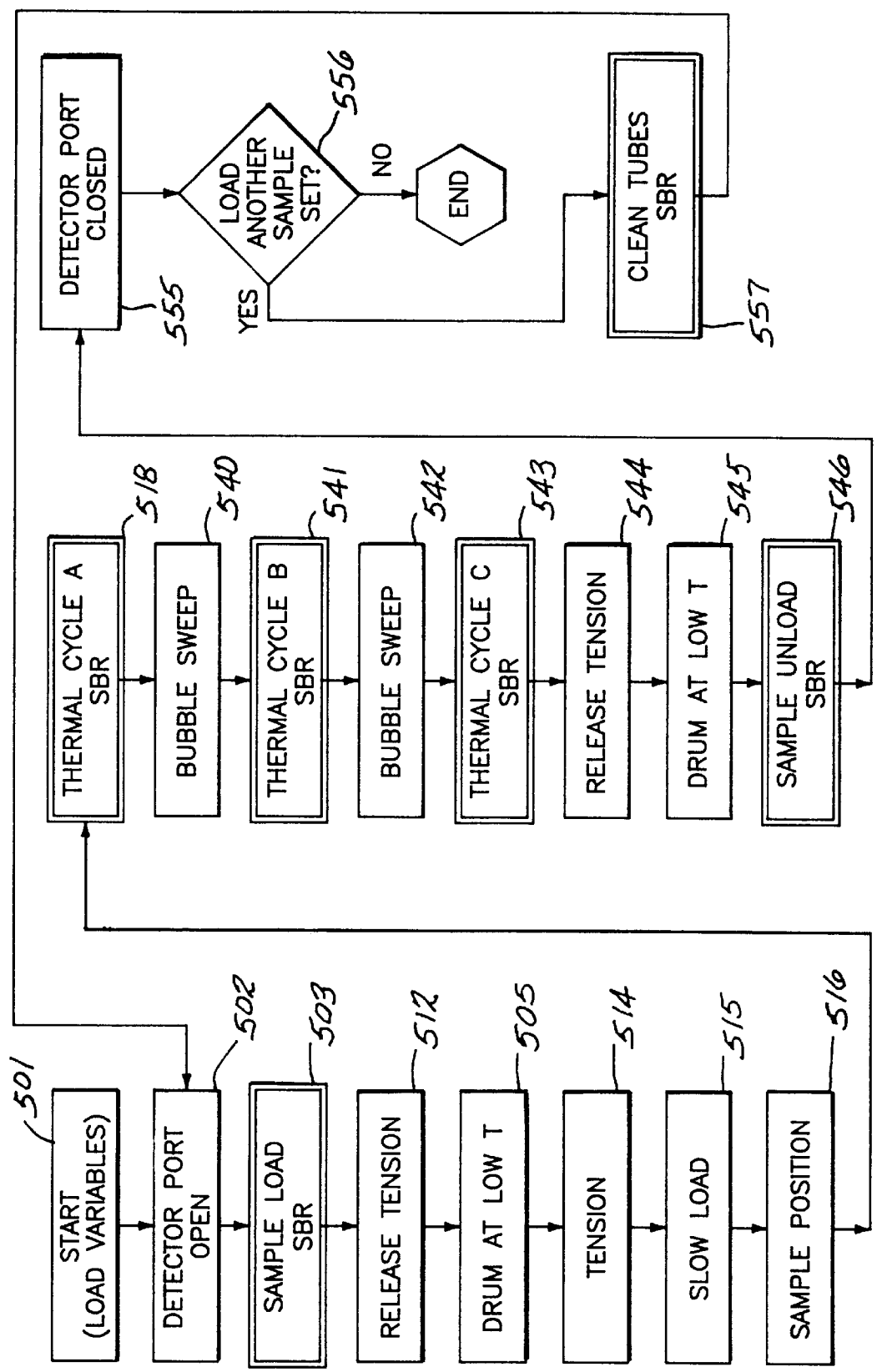
FIG. 31 is a flow diagram for the control software for the seventh embodiment of the present invention.

Referring now to FIG. 31, the user starts at block 501, and loads the required variables for the thermal cycling protocol. These variables include the denaturation temperature, annealing temperature, incubation time at the denaturation temperature, incubation time at the annealing temperature, number of cycles in thermal cycle A, B, and C, sample volume, overshoot incubation time, undershoot incubation time, the absolute pump location which correctly places the midpoint of the samples at the 6 o'clock position beneath the heat exchanger drum 300, the pump speed for load and the pump speed for unload, and the detection time. If all these variables have been entered without error, the software proceeds to block 502, and the detector port is opened to the computer 220.

Figure 32:
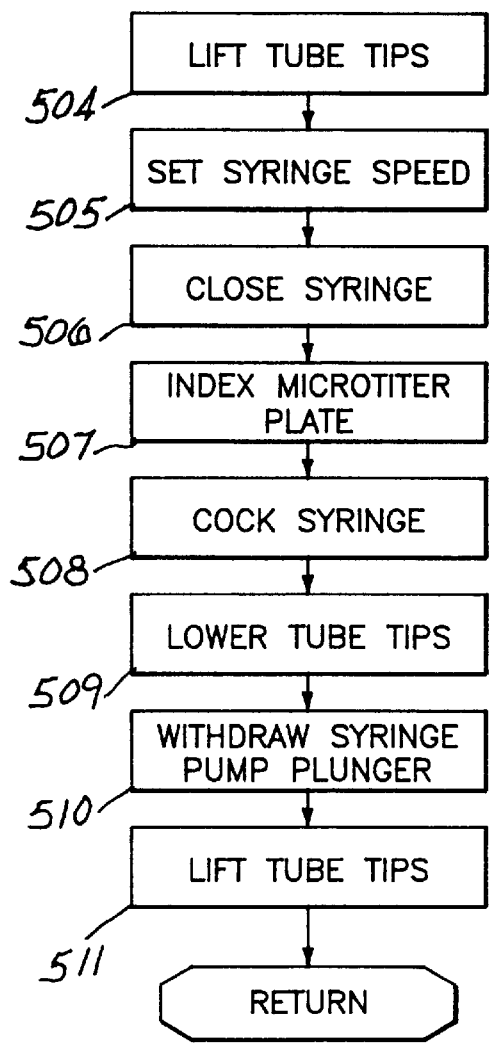
FIG. 32 is a flow diagram of the sample load subroutine portion of the diagram shown in FIG. 31.

Processing then transfers to the sample load subroutine 503 shown in FIG. 32. This subroutine 503 begins with stepper motor 242 being energized to raise the lift tube tips 238 to a position at least about a centimeter above the tubes in the microtiter tray 240. In block 505, the syringe pump 230 speed is then set. The speed of stepper motor 274 is set to withdraw the ganged syringes 262 at a predetermined rate to minimize dragout. Stepper motor 274 is actuated to close the syringe pump 230 in block 506. This action fully inserts the syringe plungers 266.

The stepper motor 248 then is energized in block 507 via bus 253 to position the microtiter plate 240 such that the first of a predetermined row of sample tubes or containers is positioned directly under the tube tips 238. Next, in block 508, syringe pump 230 is cocked. Here, the stepper motor 274 moves in the reverse direction to withdraw the plungers 266 to a slightly withdrawn position to ensure that there is a volume of air within the syringe which can be used to expel the samples completely from the tubes 228 at the end of the PCR protocol.

Computer 220 then sends a signal via bus 222 to stepper motor 242 to lower the tube tips 238 in block 509. The capillary tube tips 238 are lowered into the sample tubes almost to the bottom of the tubes. This step positions the tube tips so that a maximum volume of sample reaction mix may be withdrawn into the capillary tubes 228.

The syringe pump 230 is then actuated to withdraw preferably a 50 microliter sample, in block 510, into the capillary tubes 228. When the required volume has been withdrawn by the syringe, stepper motor 242 is then energized in block 511 to lift the tube tips 238 out of the sample tubes. This operation completes the load subroutine 503 shown in FIG. 32.

Referring back to FIG. 31, control returns to block 503 and proceeds to block 512. In block 512, stepper motor 422 is actuated to release the tension between capillary tubes 228 and the drum 300. More particularly, the stepper motor 422 rotates cam 426 to move the sliding block 406 toward the thermal cycling drum 300 a few millimeters, which is sufficient to detension the capillary tubes. Once the tension is released, in block 513, the thermal cycling drum 300 is rotated by stepper motor 318 to a position in which segment 303, which is the lowest temperature, is symmetrically positioned at the 6 o'clock position. In this position, the capillary tubes 228 fully cover the grooves 330 in this segment.

As soon as drum 300 positions segment 303 correctly at the 6 o'clock position, control proceeds to block 514. Here, stepper motor 422 is actuated again to rotate the cam 426 further out of engagement with the sliding block 406, allowing spring 410 to tension the tubes 228 against the surface of grooves 330 in this segment of the drum at the 6 o'clock position. The stepper motor 274 is then intermittently energized, in block 515, in a "slow load" fashion to move the sample from just above the capillary tube tips 238 to a position within the capillary tubes directly adjacent the segment 303 at the 6 o'clock position. This sequence of energizing stepper motor 274 to withdraw the plungers 266 a small amount and then wait for a predetermined amount of time, typically a few seconds, moves the sample in a series of forty or fifty short steps, and typically takes about two minutes to move the samples into approximate position beneath the drum 300. This intermittent motion is necessary to prevent the "dragout" phenomenon from causing the rear end of the sample volume to separate and form a bubble. Such a bubble would effectively lengthen the sample volume which could impair amplification of the nucleic acid in the sample. This slow load procedure may not be needed if the inside surface of the capillary tubes is coated with parylene or the length of capillary tubing is preheated.

Finally, in block 516, stepper motor 274 is actuated to position the samples precisely and symmetrically under the segment 303.

Figure 33:
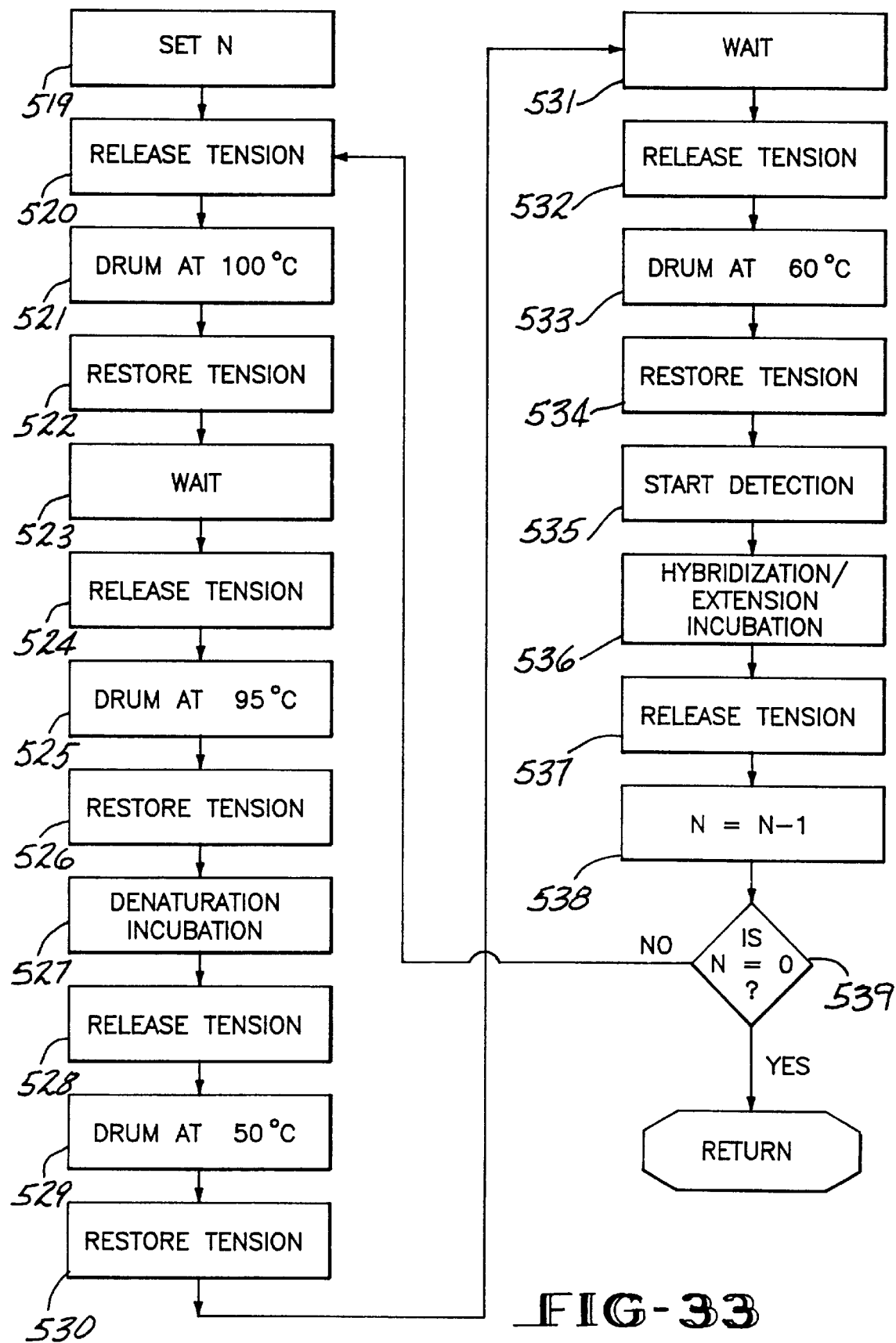
FIG. 33 is a flow diagram of the thermal cycling subroutine referred to in FIG. 31.

Referring back to FIG. 3, the thermal cycling subroutines are then performed. The thermal cycling protocol is typically 20 to 30 thermal cycles consisting of alternating denaturation incubations and annealing/extension incubations. In this breadboard design, the protocol is broken down into three sequences A, B, and C which are identical except for the number of cycles in each sequence. The block diagram of the thermal cycling subroutine shown in FIG. 33 is used for each of the sequences. First, the number of cycles to be performed in thermal cycle A is set in counter N, block 519. The tension on the capillary tubes is released in block 520 as above described by energizing stepper motor 426. Drum 300 is then rotated clockwise via stepper motor 318 to position segment 304 at the 6 o'clock position, block 521. Since the drum 300 is initially positioned with segment 303 at the 6 o'clock position, the first cycle rotation will be 180° clockwise. In subsequent cycles, rotation in block 521 will be 90° clockwise from the annealing/extension incubation position in which segment 302 is at the 6 o'clock position. The stepper motor 422 is again energized to rotate cam 426 out of engagement with sliding block 406 to retension capillary tubes 228 in block 522. Block 523 represents the required wait time with segment 304 in contact with the capillary tubes to quickly ramp the sample temperature up to the 95° C. denaturation temperature. This period is relatively short, on the order of a few seconds. The greater the temperature of the segment 304, the shorter the time required.

After the required wait period, in block 524, tension on the capillary tubes 228 is released. Drum 300 is then rotated clockwise 90°, in block 525, to position segment 306 at the 6 o'clock position. In block 526, stepper motor 422 is again energized to rotate the cam 426 and release the sliding block 406 and restore tension between capillary tubes 228 and the bottom of drum 300. This step begins the denaturation incubation symbolized in block 527. This denaturation incubation is typically on the order of one minute. At the end of this incubation, in block 528, stepper motor 422 again energizes to release the tension between the capillary tubes 228 and the drum 300. Drum 300 is then rotated 270° counterclockwise to return the cold segment 303 to the 6 o'clock position, in block 529.

The sequential clockwise rotation to 270° and return in a counterclockwise direction prevents the lead wires from the temperature controllers from becoming wound around the drum 300. When the drum 300 reaches the position in which segment 303 is at the 6 o'clock position, tension is again restored in block 530. Contact with the drum segment 303 drives the temperature of the sample quickly down to the annealing/extension temperature of 60° C. Accordingly, the wait, in block 531, is relatively short. Again, after the wait in block 531, the tension on the tubes is released, in block 532, and drum 300 is rotated clockwise 90° to position segment 302 at the 6 o'clock position. In block 534, tension is again restored between the tubes 228 and the drum 300. In block 535, fluorescence detection is begun and continues during the annealing/extension incubation for a period typically about 119 seconds. The incubation for annealing and extension is carried out in block 536. The annealing/extension incubation period and the detection period are about the same.

At the end of the annealing/extension incubation, tension is again released in block 537 between the tubes 228 and the drum 300 as above described. The counter is decremented in block 538 and queried for a null in block 539. If the counter is equal to 0, the subroutine returns to the main program, block 540. If the counter is not 0, control is directed back to block 520.

In block 540, pump 230 is actuated to push the sample back and forth and back again so that bubbles are expelled from the sample. During the continuous thermal cycling between the denaturation and annealing/extension temperatures, the sample may produce small bubbles which cause the ends of the samples to expand or move away from each other, thus moving the sample volume partially out from beneath the segment. Moving the sample back and forth by 25 microliters, 50 microliters, and then back 50 microliters has been shown to expel these bubbles from the sample, thus restoring the sample volume to its initial dimensions. Once the bubble sweep block 540 is completed, the thermal cycle B sequence is commenced as shown in block 541. Thermal cycle B is identical in operational steps to the thermal cycle A above described. Again, after the thermal cycle B, any bubbles are then swept by moving the sample back and forth in a "bubble sweep", block 542.

Typically, thermal cycle A consists of about five cycles and thermal cycle B about 10 cycles. Thermal cycle C, as shown in block 543, comprises the remaining cycles in the protocol, typically between 15 and 20, for a total of 30 to 35 cycles in the protocol. After the completion of thermal cycle C, tension between the tubes 228 and the thermal cycling drum 300 is released as indicated in block 544, and drum 300 rotated, if necessary, to position block 303 at the 6 o'clock position as in block 545.

Figure 34:
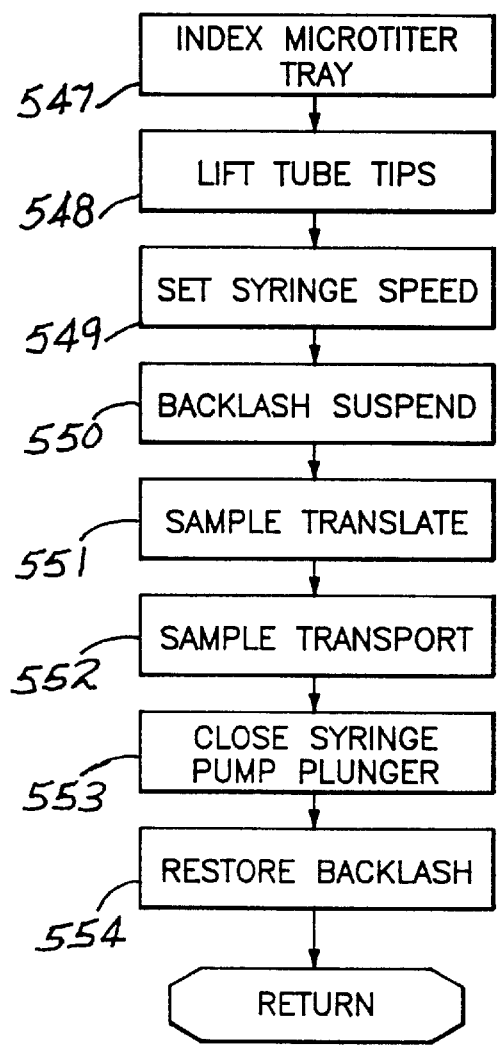
FIG. 34 is a flow diagram of the sample unload subroutine referred to in FIG. 31.

The sample unload subroutine is then performed in block 546. This subroutine is shown in FIG. 34. Initially, the capillary tube tips 238, during the thermal cycling, are in the raised position. First, the microtiter tray 240 is indexed to the next row or other row as programmed by the user, block 547. In blocks 548 and 549, a command is given to lift the capillary tube tips to the upper position and set the pump speed (stepper motor 274). The pumping speed for unload is faster than in the load subroutine because absolute positioning and dragout effects are not critical. In addition, in block 550, backlash is suspended. Backlash is a correction factor applied to stepper motor 274 to account for various tolerances which accumulate during the alternating insertion and withdrawal of the syringes. In the unload subroutine, the end position of the sample is going to be discharged from the capillary tubes. Consequently, absolute position is not important. Therefore, compensation for backlash in the pumping assembly is not required in this subroutine.

In block 551, the pump 230 (stepper motor 274) is actuated to move the sample approximately 20 millimeters from its current position at the 6 o'clock position. In block 552, the sample is then moved via pump 230 in a slow "unload" procedure, similar to the load sequence in order to prevent dragout from forming bubbles in the capillary tubing. In the slow unload procedure, the pump moves the sample approximately 8 millimeters and then waits for one second. Pump 230 then again actuates to move another 8 millimeters distance within the capillary until the sample is discharged into the sample tubes in the microtiter tray 240. Finally, in block 553, the syringe pump 230 is fully closed to push the last remaining amount of sample from the tube tips 238 into the sample tubes with the slug of air from initially cocking the syringes in block 508 of the sample load subroutine shown in FIG. 32.

Finally, in block 554, backlash is restored and, in block 555, the detector port is closed. In block 556, the program looks for a link to another sample run. If another sample run is required, a cleaning subroutine is performed, which is symbolized by block 557. This cleaning subroutine simply involves positioning the microtiter tray transfer stage 247 over the appropriate clean, rinse, or waste troughs, lowering the tube tips 238 into the cleaning tray, and aspirating a slug of cleaning solution into the capillary tubes 228 to a position beyond the heat exchanger drum 300, and oscillating the pump 230 back and forth to turbulently scrub the interior surfaces of the capillary tubes 228. The cleaning solution is then expelled into the waste trough. A rinse solution is next aspirated into the capillary tubes, oscillated back and forth, and then discharged. Finally, a conditioning solution may be aspirated into the capillary tubes in preparation for the next cycle. After this conditioning solution is discharged, the software control returns to block 502 for the next row of samples to be thermally cycled.

While the above description is illustrative of the preferred embodiments of the present invention, it will be appreciated that the inventive concept of the capillary thermal cycling apparatus in accordance with the invention may be practiced otherwise than as specifically described. For example, the various embodiments of the thermal cycling apparatus in accordance with the invention are applicable to any other nucleic acid amplification and/or reaction techniques besides PCR which requires thermal cycling at least once. The above examples are illustrative only.

These techniques include ligase chain reaction and repair chain reaction as discussed in Abramson et al., "Nucleic Acid Amplification Technologies," *Current Opinion in Biotechnology,* 1993, Vol 4, pp. 41–47. The ligase chain reaction is also discussed by Francis Barany in "The Ligase Chain Reaction in a PCR World", *PCR Methods and Applications* 1:5–16 (1991). Other methods for which the invention may be used include the 3SR method discussed by Fahy et al., "Self-sustained Sequence Replication (3SR): An Isothermal Transcription-based Amplification System Alternative to PCR", *PCR Methods and Applications* 1:25–33 (1991) and the Strand Displacement Assay (SDA) discussed by Walker et al. in "Isothermal In Vitro Amplification of DNA by a Restriction Enzyme/DNA Polymerase System", *Proc. Natl. Acad. Sci. U.S.A.* 89:392–396 (1992).

These reactions all involve reaction mixtures which undergo denaturation, annealing and extension processes. They primarily differ only in the specific extension mechanisms employed in the primer extension process in which the annealed oligonucleotides are extended to replicate the target strand. Repair chain reaction and LCR involve repetitive thermal cycling. 3SR and SDA methods involve an initial denaturation step followed by an isothermal incubation for the annealing and extension processes.

Other potential applications of the above described instruments also may include cDNA synthesis prior to PCR, ligation and kinasing of DNA, and successive enzyme treatments in which reagent additions may be required during incubations or thermal cycling. Thus, the embodiments of the invention are subject to modification, variation, and change without departing from the proper scope and fair meaning of the appended claims. Accordingly, it is intended to embrace all such changes, modifications, and variations that fall within the spirit and broad scope of the appended claims. All patent applications, patents and other publications cited herein are incorporated by reference in their entirety.

What is claimed is:

1. An apparatus for performing a nucleic acid amplification reaction in a reaction mixture in a capillary tube, the nucleic acid amplification reaction including denaturation, annealing and extension processes, the apparatus comprising:
   (a) a first heat exchanger including a thermoregulating system for stabilizing the temperature of the first heat exchanger at a temperature in a range of temperatures suitable to cause the denaturation process to occur in the reaction mixture;
   (b) a second heat exchanger including a thermoregulating system for stabilizing the temperature of the second heat exchanger at a temperature in a range of temperatures suitable for causing the annealing and extension processes to occur in the reaction mixture;
   (c) the capillary tube being routed so as to have a first portion in thermal contact with the first heat exchanger and a second portion in thermal contact with the second heat exchanger;
   (d) a valve assembly having an input port coupled to the capillary tube for receiving said reaction mixture into the tube and an output port for delivering a finished reaction product from the tube, the valve assembly allowing injection of new reaction mixture in a first position, allowing the reaction mixture to circulate in the capillary tube between the first and second heat exchangers in a second position, and allowing ejection of finished reaction product in a third position; and
   (e) a pumping device fixedly disposed in one of the heat exchangers coupled to the capillary tube so as to circulate the reaction mixture in the capillary tube such that the reaction mixture passes sequentially and cyclically through the first and second heat exchangers.

2. The apparatus of claim 1 further comprising a spectrophotometric detector optically coupled to the capillary tube for generating data representing changes in the reaction mixture during the nucleic acid amplification reaction.

3. The apparatus of claim 1 further comprising a valve means coupled to the capillary tube for providing an entry port through which reagents, additional primer, or additional enzyme may be added to the reaction mixture in the capillary tube.

4. The apparatus of claim 1 further comprising a means for injecting a discontinuity adjacent to the reaction mixture in the capillary tube.

5. The apparatus of claim 4 further comprising a cycle counter coupled to the capillary tube for counting the passage of the discontinuity.

6. The apparatus of claim 1 further comprising a computer-directed controller coupled to the pumping device and to the valve assembly for generating control signals to the pumping device and the valve assembly to automatically implement a nucleic acid amplification reaction protocol in accordance with data stored in the computer-directed controller.

7. The apparatus of claim 6 wherein the computer directed controller is user-programmable such that data defining different nucleic acid amplification reaction protocols may be entered by a user.

8. An apparatus for performing a nucleic acid amplification reaction in a reaction mixture in a capillary tube, the nucleic acid amplification reaction including denaturation, annealing and extension processes, the apparatus comprising:
   (a) a first heat exchanger including a thermoregulating system for stabilizing the temperature of the first heat exchanger at a temperature in a range of temperatures suitable to cause the denaturation process to occur in the reaction mixture;
   (b) a second heat exchanger including a thermoregulating system for stabilizing the temperature of the second heat exchanger at a temperature in a range of temperatures suitable for causing the annealing and extension processes to occur in the reaction mixture;
   (c) the capillary tube being routed so as to have a first portion in thermal contact with the first heat exchanger and a second portion in thermal contact with the second heat exchanger;
   (d) a valve assembly having an input port coupled to the capillary tube for receiving said reaction mixture into the tube and an output port for delivering a finished reaction product from the tube, the valve assembly allowing injection of new reaction mixture in a first position, allowing the reaction mixture to circulate in the capillary tube between the first and second heat exchangers in a second position, and allowing ejection of finished reaction product in a third position;
   (e) a pumping device in one of the heat exchangers coupled to the capillary tube so as to circulate the reaction mixture in the capillary tube such that the reaction mixture passes sequentially and cyclically through the first and second heat exchangers; and
   (f) a spectrophotometric detector optically coupled to the capillary tube for generating data representing changes in the reaction mixture during nucleic acid amplification reaction.

9. The apparatus of claim 8 further comprising a valve means coupled to the capillary tube for providing an entry port through which reagents, additional primer, or additional enzyme may be added to the reaction mixture in the capillary tube.

10. The apparatus of claim 8 further comprising a means for injecting a discontinuity adjacent to the reaction mixture in the capillary tube.

11. The apparatus of claim 10 further comprising a cycle counter coupled to the capillary tube for counting the passage of the discontinuity.

12. The apparatus of claim 8 further comprising a computer-directed controller coupled to the pumping device and to the valve assembly for generating control signals to the pumping device and the valve assembly to automatically implement a nucleic acid amplification reaction protocol in accordance with data stored in the computer-directed controller.

13. The apparatus of claim 12 wherein the computer directed controller is user-programmable such that data defining different nucleic acid amplification reaction protocols may be entered by a user.

14. An apparatus for performing a nucleic acid amplification reaction in a reaction mixture in a capillary tube, the nucleic acid amplification reaction including denaturation, annealing and extension processes, the apparatus comprising:
   (a) a first heat exchanger including a thermoregulating system for stabilizing the temperature of the first heat exchanger at a temperature in a range of temperatures suitable to cause the denaturation process to occur in the reaction mixture;
   (b) a second heat exchanger including a thermoregulating system for stabilizing the temperature of the second heat exchanger at a temperature in a range of temperatures suitable for causing the annealing and extension processes to occur in the reaction mixture;

(c) the capillary tube being routed so as to have a first portion in thermal contact with the first heat exchanger and a second portion in thermal contact with the second heat exchanger;

(d) a valve assembly having an input port coupled to the capillary tube for receiving said reaction mixture into the tube and an output port for delivering a finished reaction product from the tube, the valve assembly allowing injection of new reaction mixture in a first position, allowing the reaction mixture to circulate in the capillary tube between the first and second heat exchangers in a second position, and allowing ejection of finished reaction product in a third position;

(e) a pumping device in one of the heat exchangers coupled to the capillary tube so as to circulate the reaction mixture in the capillary tube such that the reaction mixture passes sequentially and cyclically through the first and second heat exchangers;

(f) means for injecting a discontinuity adjacent to the reaction mixture in the capillary tube; and (g) a cycle counter coupled to said capillary tube for counting the passage of said discontinuity.

15. The apparatus of claim 14 further comprising a valve means coupled to the capillary tube for providing an entry port through which reagents, additional primer, or additional enzyme may be added to the reaction mixture in the capillary tube.

16. The apparatus of claim 14 further comprising a computer-directed controller coupled to the pumping device and to the valve assembly for generating control signals to the pumping device and the valve assembly to automatically implement a nucleic acid amplification reaction protocol in accordance with data stored in the computer-directed controller.

17. The apparatus of claim 16 wherein the computer directed controller is user-programmable such that data defining different nucleic acid amplification reaction protocols may be entered by a user.

18. The apparatus of claim 14 wherein said cycle counter is fixedly disposed in one of said heat exchanges.

19. The apparatus of claim 14 wherein said cycle counter is a photo-electric sensor.

20. The apparatus of claim 14 wherein said cycle counter is a capacitance sensor.

* * * * *